(12) United States Patent
Iyer et al.

(10) Patent No.: US 8,404,651 B2
(45) Date of Patent: Mar. 26, 2013

(54) COMPOSITIONS AND METHODS FOR TREATING VIRAL INFECTIONS

(75) Inventors: Radhakrishnan P. Iyer, Shrewsbury, MA (US); Seetharamaiyer Padmanabhan, Lexington, MA (US)

(73) Assignee: Spring Bank Pharmaceuticals, Inc., Milford, MA (US)

( * ) Notice: Subject to any disclaimer, the term of this patent is extended or adjusted under 35 U.S.C. 154(b) by 3 days.

(21) Appl. No.: 12/897,389

(22) Filed: Oct. 4, 2010

(65) Prior Publication Data

US 2011/0207690 A1 Aug. 25, 2011

Related U.S. Application Data

(63) Continuation of application No. PCT/US2009/039424, filed on Apr. 3, 2009.

(60) Provisional application No. 61/072,794, filed on Apr. 3, 2008, provisional application No. 61/072,799, filed on Apr. 3, 2008, provisional application No. 61/074,421, filed on Jun. 20, 2008.

(51) Int. Cl.
*A01N 43/04* (2006.01)
*A61K 31/70* (2006.01)
(52) U.S. Cl. ............... 514/43; 514/45; 514/46; 514/47; 514/48; 514/49; 514/50; 514/51
(58) Field of Classification Search .................. None
See application file for complete search history.

(56) References Cited

U.S. PATENT DOCUMENTS

2004/0158054 A1  8/2004  Wu et al.

FOREIGN PATENT DOCUMENTS

| WO | 94/26764 A1 | 11/1994 |
| WO | 98/07734 A1 | 2/1998 |
| WO | 2007/070598 A2 | 6/2007 |
| WO | 2007/149462 A2 | 12/2007 |

OTHER PUBLICATIONS

Lincoln et al. HIV Medicine (2003), vol. 4, pp. 241-249.*
R.P. Iyer et al., "Acyloxyaryl Prodrugs of Oligonucleoside Phosphorothioates", Bioorganic & Medicinal Chemistry Letters, 6(16), pp. 1917-1922 (1996).
R.P. Iyer et al., "Phosphorothioate Di- and Trinucleotides as a Novel Class of Anti-Hepatitis B Virus Agents", Antimicrobial Agents and Chemotherapy, 48(6), pp. 2199-2205 (2004).
L. Franchi et al., "Function of Nod-like receptors in Microbial Recognition and Host Defense", Immunol. Rev., 227(1), pp. 106-128 (2009).
R.P. Iyer et al., "Anti-Hepatitis B Virus Activity of ORI-9020, a Novel Phosphorthioate Dinucleotide, in a Transgenic Mouse Model", Antimicrobial Agents and Chemotherapy, 48(6), pp. 2318-2320 (2004).
A. Sabbah et al., "Activation of innate immune antiviral response by NOD2", Nat. Immunol., 10(10), pp. 1073-1080 (2009).
M.U. Gack et al., "Roles of RIG-I N-terminal tandem CARD and splice variant in TRIM25-mediated antiviral signal transduction", PNAS USA, 105(43), pp. 16743-16748 (2008).
K. Takeda et al., "Toll-like receptors in innate immunity", International Immunology, 17(1), pp. 1-14 (2005).
National Institutes of Health Consensus Development Conference Statement: Management of hepatitis C, http://consensus.nih.gov/2002/2002HepatitisC2002116html.htm; Hepatology, 36, S4-S20 (2002).
R.P. Iyer et al., "Rapid Functionalization and Loading of Solid Supports", Org. Prep. Proced. Int., 37(3), pp. 205-212 (2005).
S. Myong et al., "Cytosolic Viral Sensor RIG-1 is a 5'-Triphosphate-Dependent Translocase on Double-Stranded RNA", Science, vol. 323, pp. 1070-1074 (2009).
S. Akira et al., "Pathogen Recognition and Innate Immunity", Cell, vol. 124, pp. 783-801 (2006).
M.G. Katze et al.. "Viruses and Interferon: A Fight for Supremacy", Nature Reviews, vol. 2, pp. 675-687 (2002).
T. Saito et al., "Regulation of innate antiviral defenses through a shared repressor domain in RIG-1 and LGP2", PNAS USA, 104(2), pp. 582-587 (2007).
S. Cui et al., "The C-Terminal Regulatory Domain is the RNA 5'-Triphosphate Sensor of RIG-1", Molecular Cell, vol. 29, pp. 169-179 (2008).
M. Yoneyama et al., The RNA helicase RIG-1 has an essential function in double-stranded RNA-induced innate antiviral responses, Nature Immunology, 5(7), pp. 730-737 (2004).
R.P. Iyer et al., "Microwave-Assisted Functionalization of Solid Supports for Rapid Loading of Nucleosides", Current Protocols Unit 3.13 (Beaucage et al. Eds.) John Wiley and Sons (2006).
R.P. Iyer et al., "RNA interference: an exciting new approach for target validation, gene expression analysis and therapeutics", Drugs of the Fugure, 28(2) (2003).
S. Padmanabhan et al., "Microwave-assisted functionalization of solid supports: application in the rapid loading of nucleosides on controlled-pore-glass (CPG)", Tetrahedron Letters, pp. 343-347 (2004).
N. Dias et al., "Antisense Oligonucleotides: Basic concepts and Mechanisms", Molecular Cancer Therapeutics, vol. 1, pp. 347-355 (2002).

(Continued)

*Primary Examiner* — Patrick Lewis
(74) *Attorney, Agent, or Firm* — Edwards Wildman Palmer LLP; Peter F. Corless; Weiying Yang

(57) ABSTRACT

The present invention provides compositions methods for treating susceptible viral infections, especially hepatitis C viral (HCV) infections as well as co infections of HCV with other viruses such as HBV and/or HIV. In one embodiment, the present invention provides compositions having the formula (I) and their use in treating viral infections:

$$V-M-J-(CR_4R_5)_n-A-(CR_2R_3)_n-W-\underset{\underset{N_2-(Q)_m}{|}}{\overset{\overset{N_1}{|}}{\underset{|}{P}}}=Z \quad (I)$$

or a pharmaceutically acceptable salt, ester, stereoisomer, tautomers, solvate, prodrug, or combination thereof.

6 Claims, No Drawings

OTHER PUBLICATIONS

V. Hornung et al., "5'-Triphosphate RNA is the Ligand for RIG-1", Science, vol. 314, pp. 994-997 (2006).

A. Pichlmair et al., "RIG-1 Mediated Antibiral Responses to Single-Stranded RNA Bearing 5'-Phosphates", Science, vol. 314, pp. 997-1001 (2006).

E. Meylan et al., "Cardif: A Protein Central to Innate Immunity is Inactivated by the HCV NS3 Serine Protease", Hepatology, 43(3), pp. 615-617 (2006).

World Health Organization Report: Viral Hepatits: Report by the Secretariat, 63rd World Health Assembly (2010).

Y. Jin et al., "Parallel Solid-Phase Synthesis of Nucleoside Phosphoramidate Libraries", Bioorganic & Medicinal Chemistry Letters 11, pp. 2057-2060 (2001).

Y. Jin et al., "Synthesis and Antiviral Evaluation of Nucleic Acid-Based (NAB™) Libraries", Bioorganic & Medicinal Chemistry Letters 10, pp. 1921-1925 (2000).

British Examination Report dated May 15, 2012 issued in the corresponding British Application No. GB1018497.6.

* cited by examiner

COMPOSITIONS AND METHODS FOR TREATING VIRAL INFECTIONS

RELATED APPLICATION

This application is a continuation of International Application No. PCT/US2009/039424, which designated the United States and was filed on Apr. 3, 2009, published in English, which claims the benefit of U.S. Provisional Application No. 61/072,794, filed on Apr. 3, 2008; U.S. Provisional Application No. 61/072,799 filed Apr. 3, 2008; and U.S. Provisional Application No. 61/074,421, filed on Jun. 20, 2008. The entire teachings of the above applications are incorporated herein by reference.

BACKGROUND OF THE INVENTION

Over 170 million people worldwide are infected by Hepatitis C Virus. The current therapies have dose-limiting toxicity and there exists significant unmet medical need. Several compounds are under development that target HCV polymerase, HCV protease and HCV NS5A. However, the viral replication cycle is significantly error-prone resulting in emergence of resistant mutants particularly under the selective pressure of antiviral therapy. This presents significant challenges to developing antiviral treatment regimens.

To date most anti-HCV agents that have been developed are HCV polymerase inhibitors. An NS3 protease inhibitor BILN-2061 was the first compound tested in humans that produced significant viral load reduction in patients. A nucleoside analog NM 283 showed antiviral effect in HCV-infected patients. However significant drug resistance and toxicity have been already noted with a few compounds in the clinic. Several antiviral compounds are under clinical development. For example, non-nucleoside benzothiadiazines, acyl pyrrolidines, benzofurans, Phenyl alanines, substituted thiophene, dihydropyranones, pyranoindoles, benzimidazoles and indole have been found to be inhibitors of NS5B polymerase domain. However, in vitro replicon assays reveal significant cross resistance with different drugs.

Because resistance development to antiviral drugs is virtually certain, one way to combat it has been combination treatments including drugs that may not promote cross-resistant mutants. Usually drugs that effect different viral enzymes do not show cross resistance and can be used in combinations successfully. Thus, a combination of different drugs with different mechanisms of action, which are not cross-resistant, will be the key to successful antiviral therapy.

Shorter chain oligonucleotides (less than 8-mers) with lesser number of charges and smaller molecular weight compared to 20-mer oligonucleotides represent a promising class of novel molecules with potential therapeutic properties as antivirals. Indeed, recent reports suggest that mono-, di-, tri-, and short chain oligonucleotides possess significant biological activity that can be exploited for various therapeutic applications. However, improved short oligonucleotides having improved properties for oral, transdermal or other non-invasive modes of delivery to the patient are still needed for use as stand alone therapeutics or in combination therapies.

SUMMARY OF THE INVENTION

The present invention provides compositions and methods for treating susceptible viral infections, especially hepatitis C viral (HCV) infections as well as co-infections of HCV with other viruses such as HBV and/or HIV. In one embodiment, the present invention provides compositions having the formula (I) and their use in treating viral infections:

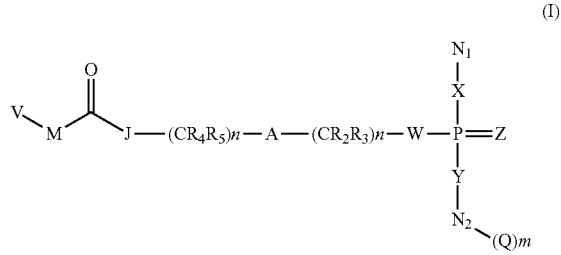

(I)

or a pharmaceutically acceptable salt, ester, stereoisomer, tautomers, solvate, prodrug, or combination thereof, wherein:

$N_1$ and $N_2$ are independently selected from naturally occurring nucleosides or modified nucleosides;

W, X, Y and Z are each independently selected from O, S and $NR_1$ wherein $R_1$ is independently selected from hydrogen, substituted or unsubstituted aliphatic and substituted or unsubstituted aromatic;

$R_2$, $R_3$, $R_4$ and $R_5$ are each independently selected from hydrogen, substituted or unsubstituted aliphatic group and substituted or unsubstituted aromatic group;

n is 0, 1, 2, 3, 4 or 5;

A is absent, or substituted or unsubstituted aromatic group;

J is absent, $CR_6R_7$, O, S or $NR_1$ wherein $R_6$ and $R_7$ are each independently selected from hydrogen, substituted or unsubstituted aliphatic group and substituted or unsubstituted aromatic group and $R_1$ is as defined above;

M is absent, $CR_8R_9$, O, S or $NR_1$ wherein $R_8$ and $R_9$ are each independently selected from hydrogen, substituted or unsubstituted aliphatic group and substituted or unsubstituted aromatic group and $R_1$ is as defined above;

V is substituted or unsubstituted aliphatic group or substituted or unsubstituted aromatic group;

Q is absent, or a modified or unmodified nucleotide; and m is 1, 2, 3 or 4.

DETAILED DESCRIPTION OF THE INVENTION

The present invention provides short nucleotide compositions and methods for treating susceptible viral infections, especially hepatitis C viral infections. The term "short nucleotide(s)" refers to a mononucleotide, dinucleotide or polynucleotide formed from 1 to about 6 linked nucleoside units. The invention also encompasses mononucleoside compounds. The term "susceptible viral infections" as used herein means viral infections caused by a wide range of RNA and DNA viruses, including, but not limited to, the families of viruses such as flaviviruses-including the genus flavivirus, pestivirus of which Kunjin virus is a member, and hepavirus of which hepatitis C virus is a member, and arbovirus of which the West Nile virus is a member, orthomyxoviruses, paramyxoviruses, arenaviruses, bunyaviruses, herpes viruses, adenoviruses, poxviruses, and retroviruses. Typical suitable "susceptible viral infections" include influenza A and B viral infections; parainfluenza viral infections, respiratory syncytial virus ("RSV") infections such as RSV bronchiolitis and RSV pneumonia especially such RSV infections in children and infants as well as RSV pneumonia in patients with preexisting cardiopulmonary disease, measles viral infections, Lassa fever viral infections, Korean Haemorrhagic fever infections, hepatitis B viral (HBV) infections, Crimean Congo-Haemorrhagic and HCV infections and HIV-1 infections, encephalitis infections such as caused by West Nile virus or Kunjin virus or the St. Louis encephalitis infections, as well as viral infections found in immunocompromised patients. Other susceptible viral infections are disclosed in U.S. Pat. No. 4,211,771 at column 2, line 21 to column 3 line 37; doses and dose regimens and formulations are disclosed at column 3, line 4 to column 9, line 5. In one embodiment, the viral infection is not solely an HBV infection, however, the viral infection may be an HBV co-infection with another virus such as HCV.

The compositions of the invention suitable for treating susceptible viral infections and particularly HCV infections as well as co infections of HCV with other viruses such as HBV and/or HIV, are represented by compounds of formulas I-IV. It should be noted that in some of the following formulas, a nucleoside unit is represented by the internationally accepted convention of line drawing. In the example below a 2'-substituted ribonucleoside is represented in both the conventional structure and the corresponding line drawing format:

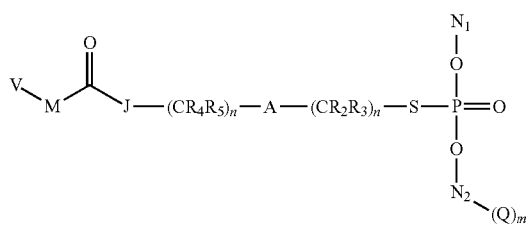

(II)

Wherein V, M, J, A, $R_2$, $R_3$, $R_4$, $R_5$, $N_1$, $N_2$, Q, m and n are as previously defined in formula I.

Representative compounds according to the invention are those selected from the group consisting of: Compounds (1)-(8) of the formula A1:

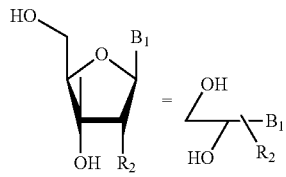

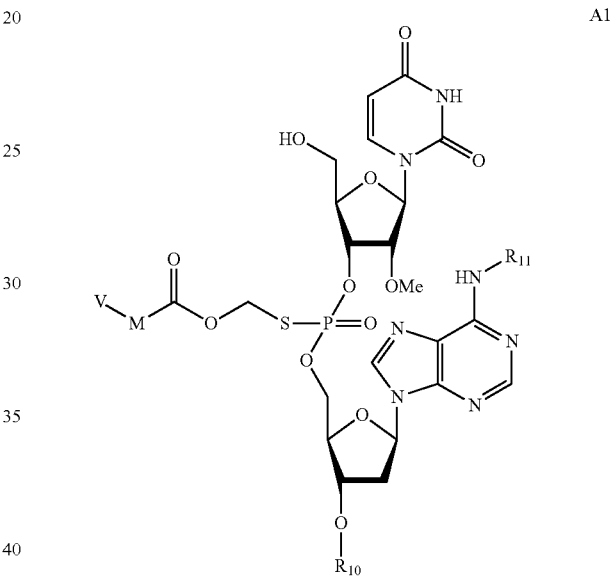

A1

The sugar units attached to $B_1$ and $B_2$ that give rise to α or β N- or C-nucleoside includes, but is not limited to, furanose, deoxyribofuranose, ribose, and arabinose.

In a first embodiment, the compounds of the present invention are compounds represented by formula I illustrated above, or racemates, enantiomers, diastereomers, geometric isomers, tautomers thereof.

A preferred subgenera of formula I are compounds represented by formula (II) as illustrated below, or racemates, enantiomers, diastereomers, geometric isomers, tautomers thereof.

Wherein V, M, $R_{10}$ and $R_{11}$ are delineated for each example in Table 1.

TABLE 1

| Compound No. | V | M | $R_{10}$ | $R_{11}$ |
|---|---|---|---|---|
| 1 | (isopropyl) | absent | H | H |
| 2 | (isopropyl) | O | H | H |

TABLE 1-continued

| Compound No. | V | M | $R_{10}$ | $R_{11}$ |
|---|---|---|---|---|
| 3 | (5β-cholane-3α,12α-diol moiety) | absent | H | H |
| 4 | butyl-O-CH₂CH₂- | O | H | H |
| 5 | butyl-O-CH₂CH₂- | O | C(O)Ph | H |
| 6 | butyl-O-CH₂CH₂- | O | H | C(O)Ph |
| 7 | H₂N-CH(CH₂Ph)- | absent | H | H |
| 8 | bis(methoxy-hydroxyphenyl-CH=CH-CO-)CH- (curcumin-like) | O | H | H |

Representative compounds according to the invention are those selected from the group consisting of:
Compounds (9)-(16) of the formula B1:

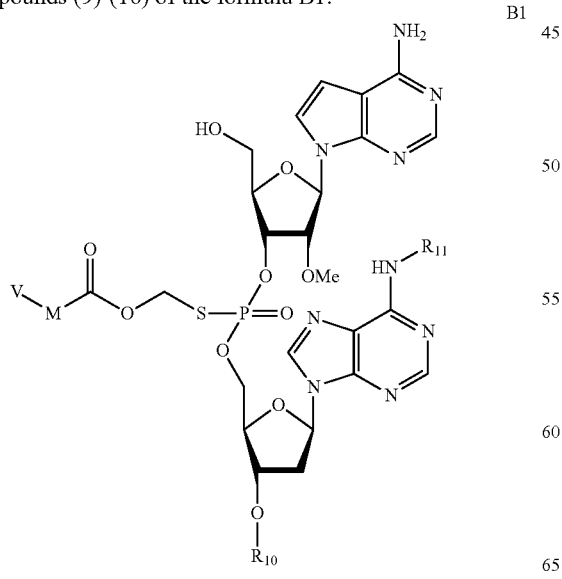

wherein V, M, $R_{10}$ and $R_{11}$ are delineated for each example in Table 2.

TABLE 2

| Compound No. | V | M | $R_{10}$ | $R_{11}$ |
|---|---|---|---|---|
| 9 | *tert*-butyl group | absent | H | H |
| 10 | isopropyl group | O | H | H |
| 11 | cholic acid-derived steroid moiety (3,12-dihydroxy) | absent | H | H |
| 12 | butoxypropyl group (CH₃CH₂CH₂CH₂-O-CH₂CH₂CH₂-) | O | H | H |
| 13 | butoxypropyl group | O | C(O)Ph | H |
| 14 | butoxypropyl group | O | H | C(O)Ph |
| 15 | H₂N-CH(CH₂Ph)-CH₂- group | absent | H | H |
| 16 | bis-(4-hydroxy-3-methoxycinnamoyl) methylene group (HO-C₆H₃(OCH₃)-CH=CH-CO-CH(H)-CO-CH=CH-C₆H₃(OCH₃)-) | O | H | H |

Examples of compounds of formula I include but are not limited to:

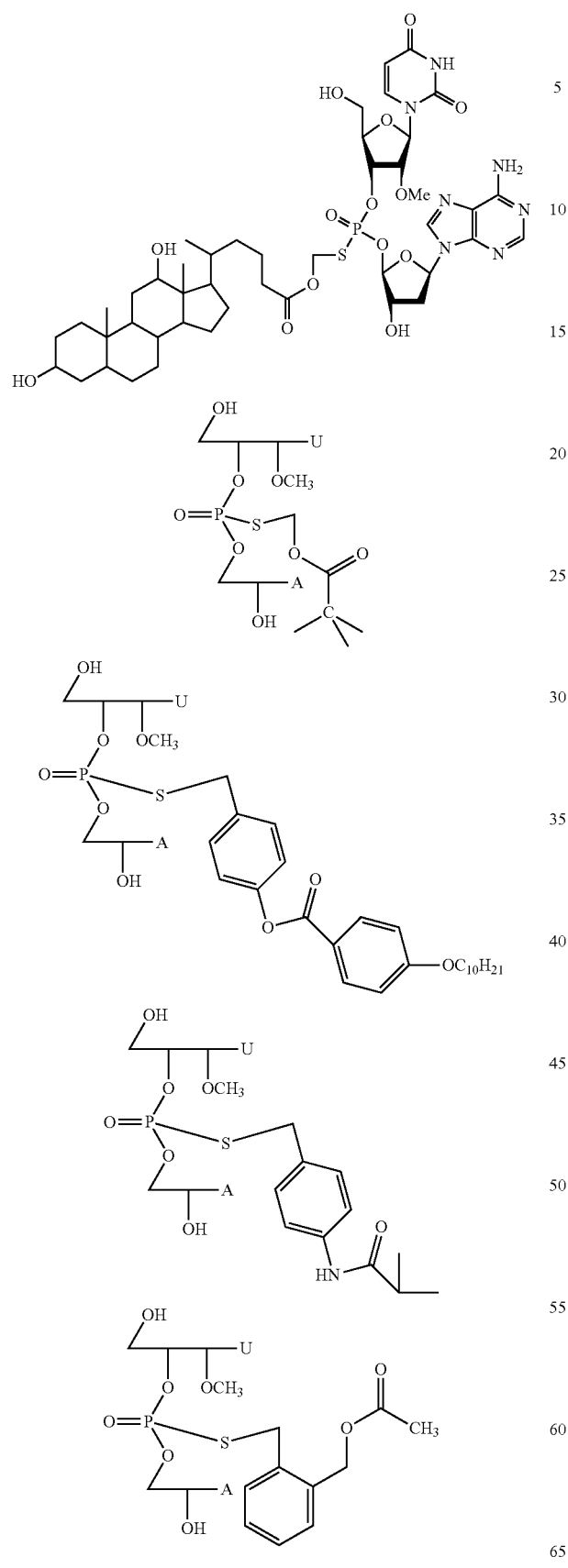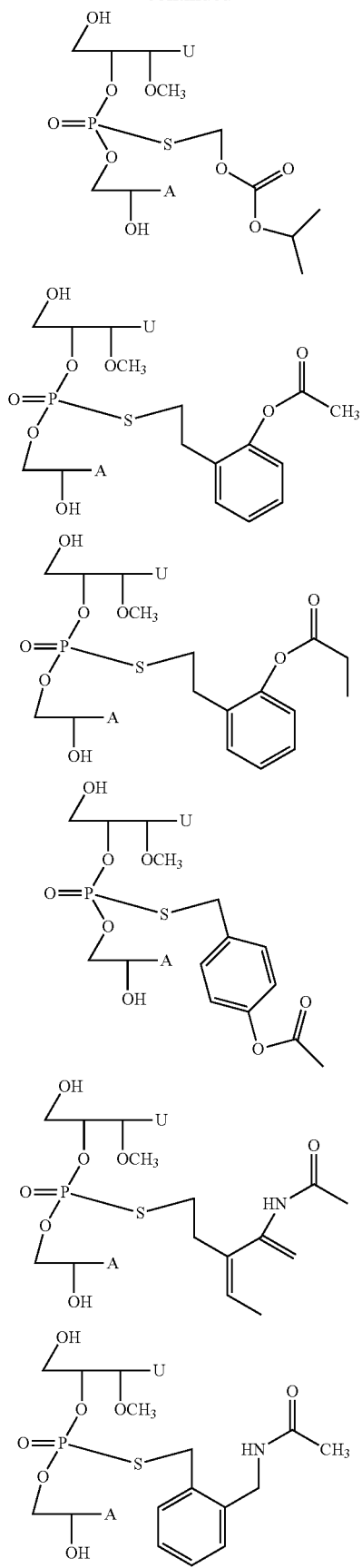

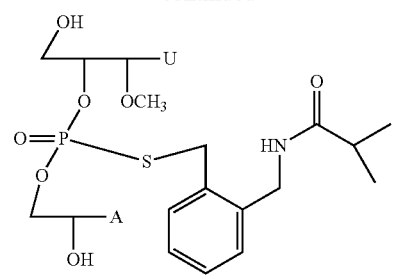
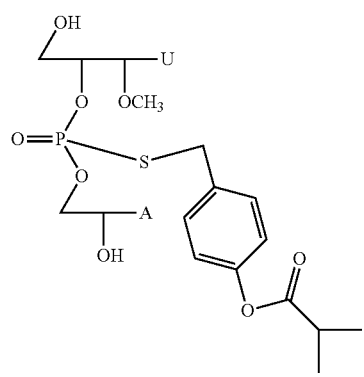
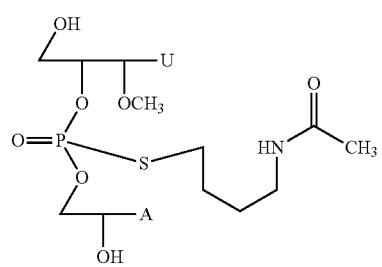
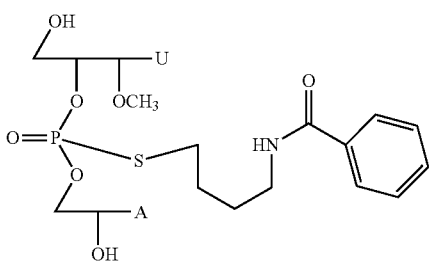
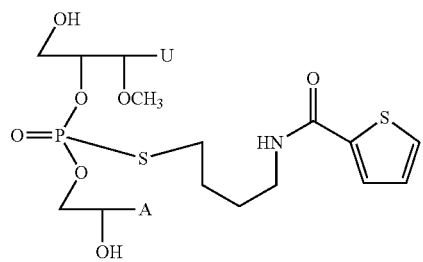
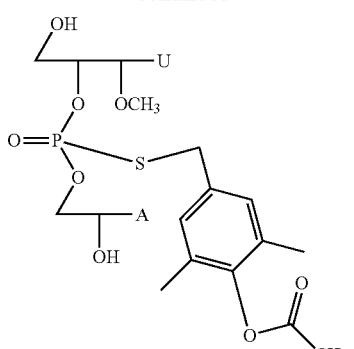
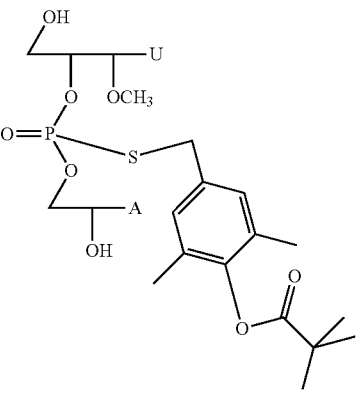
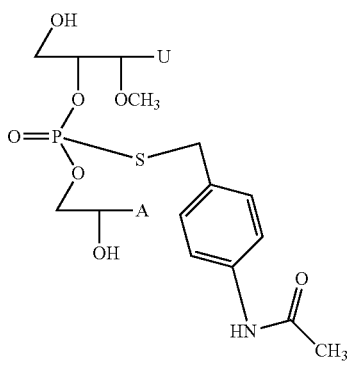
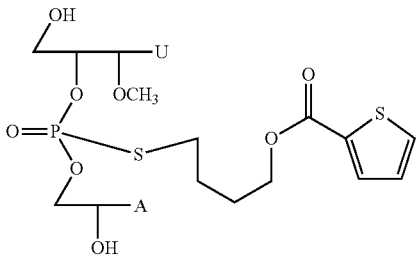
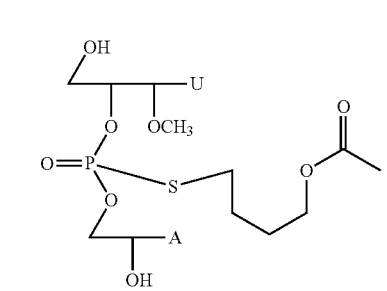

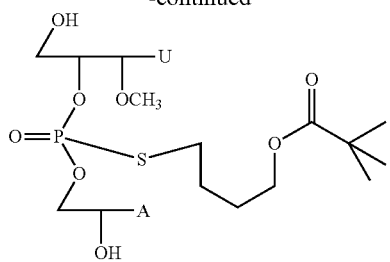
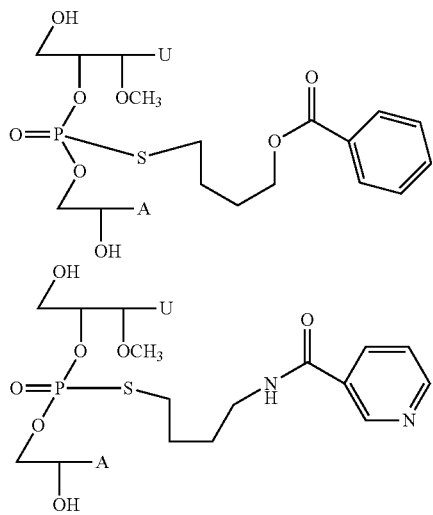
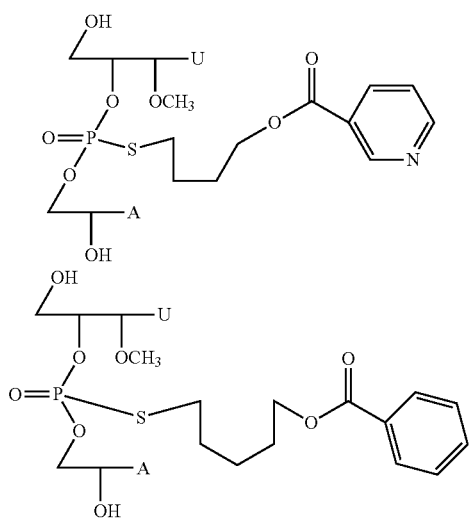
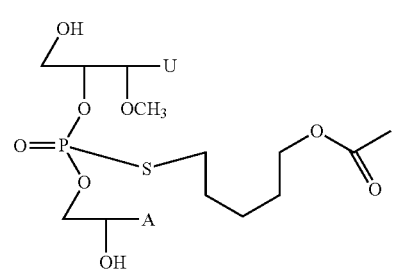
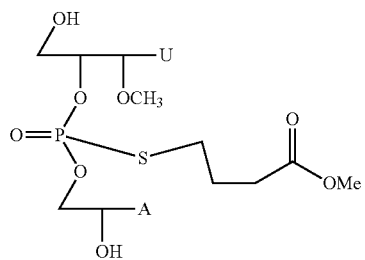
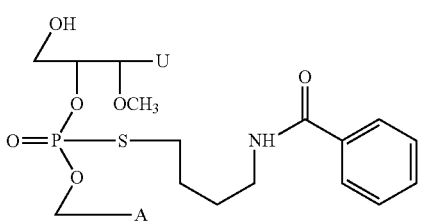
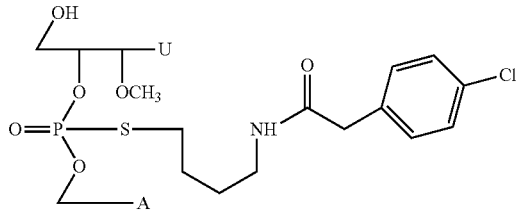
Other examples of compounds of Formula I include but are not limited to:
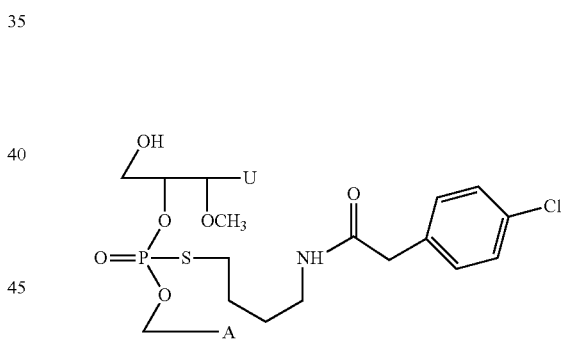
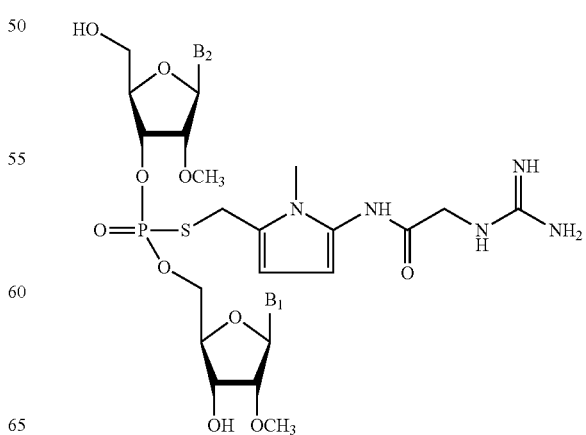

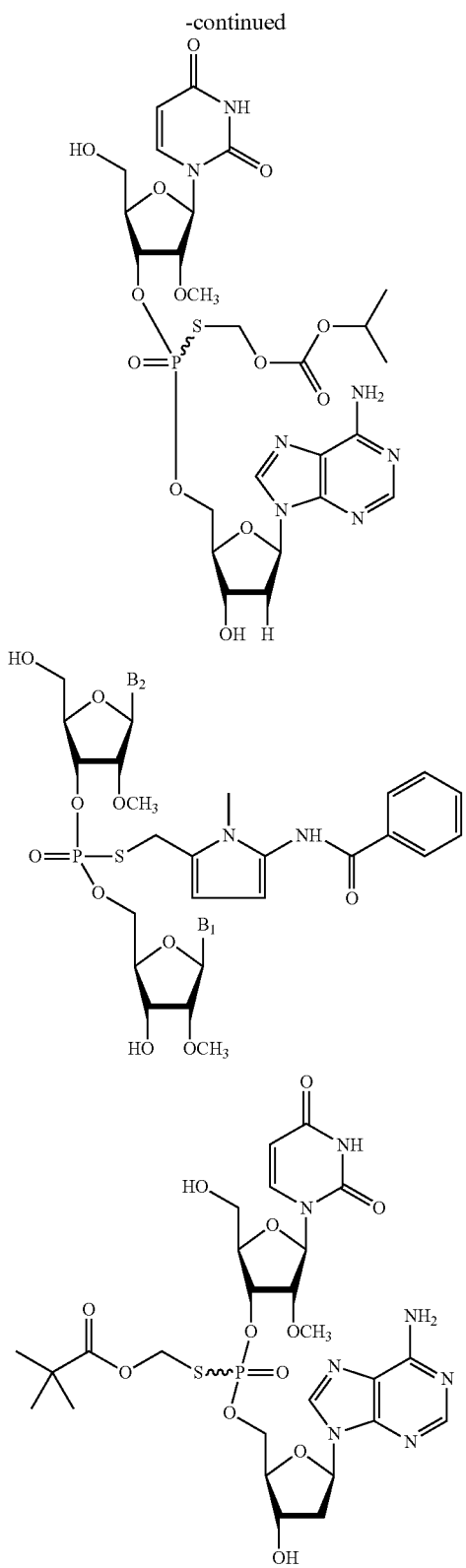

or a pharmaceutically acceptable salt, ester, stereoisomer, tautomer, solvate, prodrug, or combination thereof, wherein:

M' and M" are each independently selected from $CH_2$, NH, NR", O, and S; wherein R" is substituted or unsubstituted aliphatic group or substituted or unsubstituted aromatic group;

X' is O, NH, NR", or S; wherein R" is as previously defined;

Y' is $OR_{12}$, $NHR_{12}$, and $SR_{12}$; where each $R_{12}$ is independently selected from H, substituted or unsubstituted aliphatic group or substituted or unsubstituted aromatic group;

Z' and Z" are each independently O, $NR_{13}$, and S; where $R_{13}$ is H, substituted or unsubstituted aliphatic group or substituted or unsubstituted aromatic group;

R and R' are each independently H, OH, O-alkyl, O-aryl, O-heteroaryl, O-aralkyl, O-alkyl heteroaryl, $-NH_2$, $-NHR_{14}$, $-NR_{15}NR_{16}$, substituted or unsubstituted alkyl, substituted or unsubstituted cycloalkyl, substituted or unsubstituted aryl, substituted or unsubstituted aralkyl, or substituted or unsubstituted heterocyclic, wherein $R_{14}$, $R_{15}$ and $R_{16}$ are each independently selected from H, substituted or unsubstituted aliphatic group or substituted or unsubstituted aromatic group;

$B_1$ and $B_2$ are each independently selected from absent, H, naturally occurring nucleobases and modified bases; and Q' is absent or

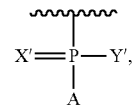

wherein X' and Y' are as previously defined and A is OH, O-alkyl, O-aryl, O-heteroaryl, O-aralkyl, or O-alkyl heteroaryl.

In a preferred embodiment, at least one of $B_1$ and $B_2$ are independently the following formula:

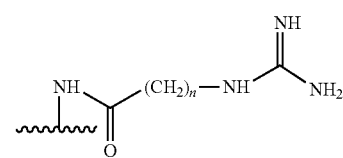

wherein $B_1$ and $B_2$ are naturally occurring nucleobases or modified bases.

In another embodiment, the present invention provides compounds having the formula (III) and their use in treating viral infections:

Specific examples of compounds of Formula III include but are not limited to:
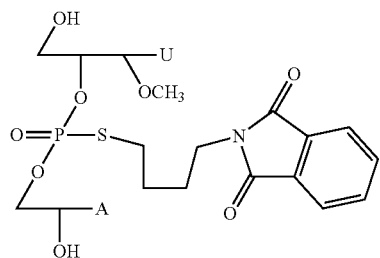
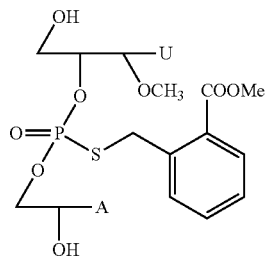
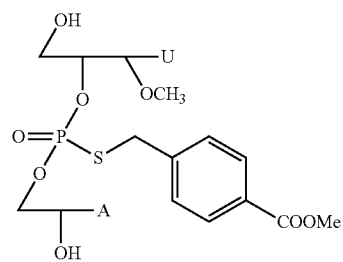
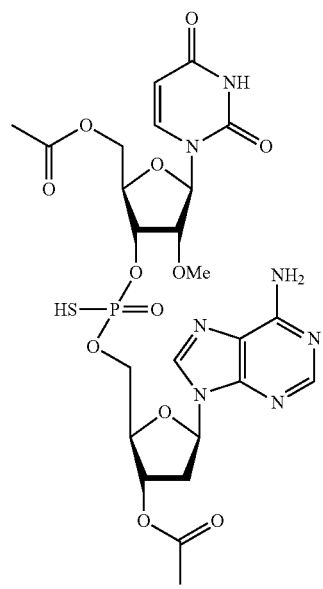
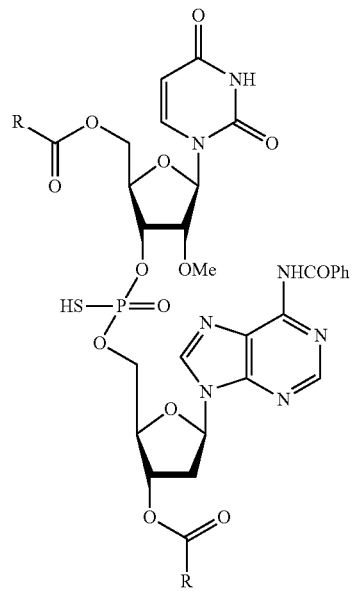
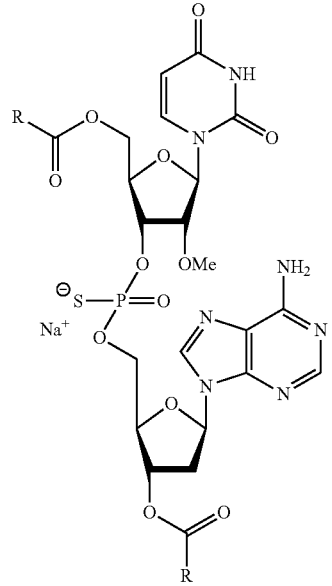
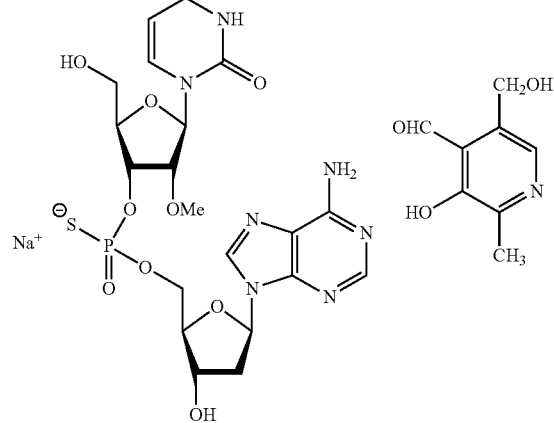

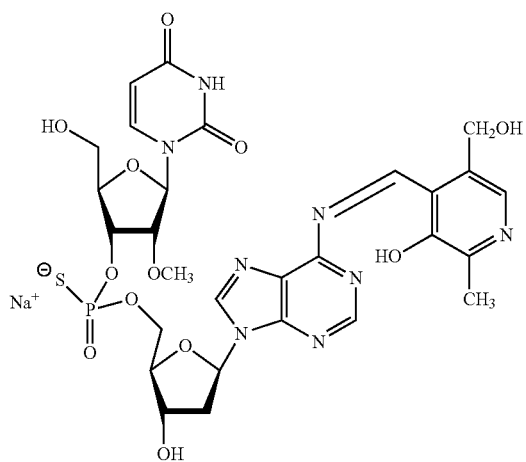
wherein in the above formulas R is a substituted or unsubstituted aliphatic group having a backbone of up to ten atoms and preferably, R is a long chain fatty acid.
Additional compounds of formula III include but are not limited to the following:
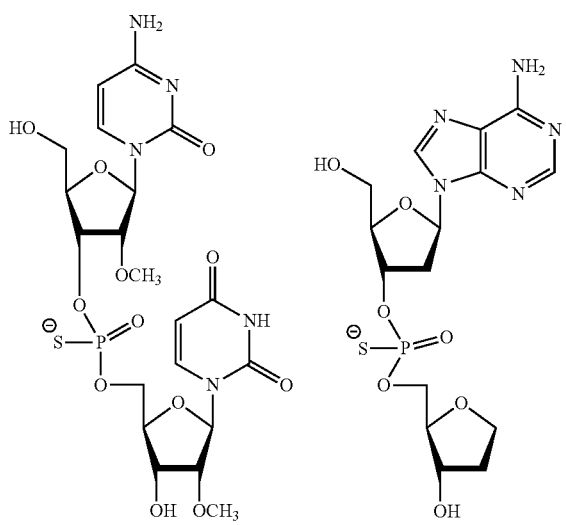
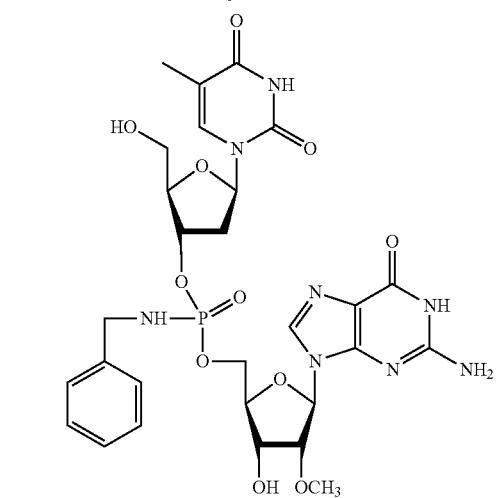
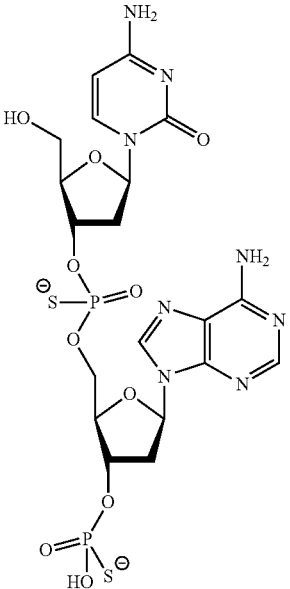
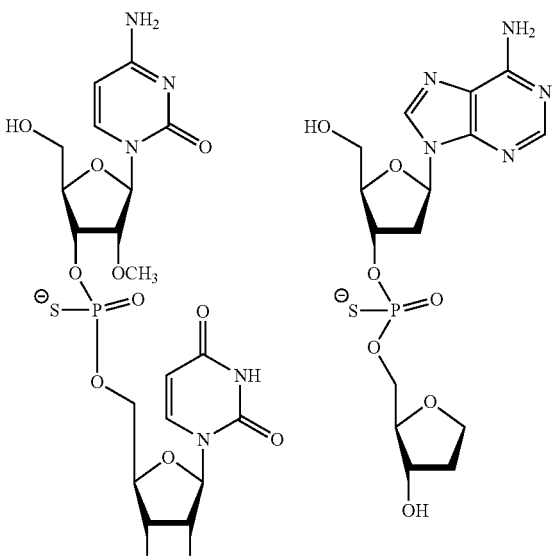
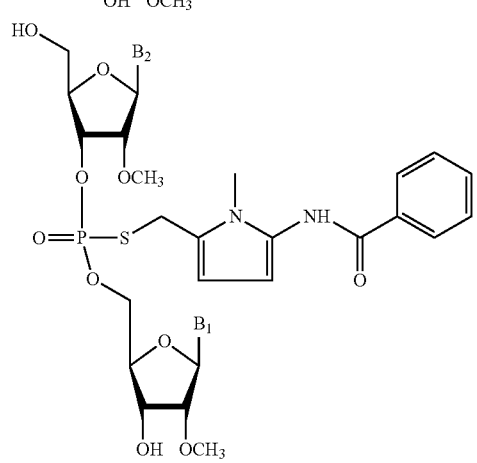
wherein in those above formulas $B_1$ and $B_2$ are independently naturally occurring nucleobases or modified bases.

In another embodiment, the present invention provides compounds having the formula (IV) and their use in treating viral infections:

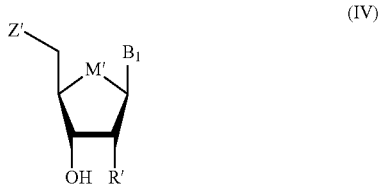

(IV)

M' is selected from $CH_2$, NH, NR", O, and S; wherein R" is substituted or unsubstituted aliphatic group or substituted or unsubstituted aromatic group;

X is O, NH, NR", or S where R" is previously defined;

Z' is H, OH, OR", $OR_{17}$, COOH, COOR", $NH_2$, NHR", $NHR_{17}$ where R" is previously defined and $R_{17}$ is aroyl (CO—Ph), sulfonyl ($SO_2$—R), ureidyl (CO—NH—R), thioureidyl (CS—NH—R) wherein R is selected from hydrogen, substituted or unsubstituted aliphatic group and substituted or unsubstituted aromatic group, however when M' is O, Z' is not OH;

R' is H, OH, O-alkyl, O-aryl, O-heteroaryl, O-aralkyl, O-alkyl heteroaryl, O-aroyl, —$NH_2$, —$NHR_1$, —$NR_1NR_2$ alkyl, substituted alkyl, cycloalkyl, aryl, substituted aryl, aralkyl, or heterocylic wherein $R_1$ and $R_2$ are each independently selected from hydrogen, substituted or unsubstituted aliphatic group and substituted or unsubstituted aromatic group, however when M' is O, R' is not OH;

$B_1$ is H, a naturally occurring nucleobase or a modified base.

In a preferred embodiment, R, $R_1$ and $R_2$ of formula IV are substituted or unsubstituted alkyl, substituted or unsubstituted cycloalkyl, substituted or unsubstituted aryl, substituted or unsubstituted aralkyl, or substituted or unsubstituted heterocyclic.

Non limiting examples of compounds of formula (IV) include:

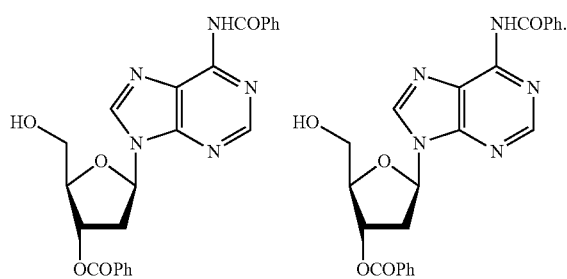

Listed below are definitions of various terms used to describe this invention. These definitions apply to the terms as they are used throughout this specification and claims, unless otherwise limited in specific instances, either individually or as part of a larger group.

An "aliphatic group" is non-aromatic moiety that may contain any combination of carbon atoms, hydrogen atoms, halogen atoms, oxygen, nitrogen, sulfur or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. It is understood that any alkyl, alkenyl, alkynyl and cycloalkyl moiety described herein can also be an aliphatic group, an alicyclic group or a heterocyclic group. Such aliphatic groups may be further substituted.

The term "aryl," as used herein, refers to a mono- or polycyclic carbocyclic ring system including, but not limited to, phenyl, naphthyl, tetrahydronaphthyl, indanyl, idenyl. The term aryl includes, but is not limited to, bicyclic aryls or bicyclic heteroaryls having a ring system consisting of two rings wherein at least one ring is aromatic. The term aryl includes, but is not limited to, tricyclic aryls or tricyclic heteroaryls having a ring system consisting of three rings wherein at least one ring is aromatic.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl.

In accordance with the invention, any of the aryls, substituted aryls, heteroaryls and substituted heteroaryls described herein, can also be any aromatic group. Therefore, the term "aromatic group" as used herein includes all such aryls, substituted aryls, heteroaryls and substituted heteroaryls. Aromatic groups can be substituted or unsubstituted.

The term "alkyl," as used herein, refers to saturated, straight- or branched-chain hydrocarbon radicals containing one or more carbon atoms and preferably contain 1-24 carbon atoms. Examples of alkyl radicals include, but are not limited to, methyl, ethyl, propyl, isopropyl, n-butyl, tert-butyl, neopentyl, n-hexyl, heptyl and octyl radicals, decyl, dodecyl radicals.

The term "alkenyl," as used herein, refer to straight- or branched-chain hydrocarbon radicals containing at least two and preferably from two to eight carbon atoms having at least one carbon-carbon double bond by the removal of a single hydrogen atom. Alkenyl groups include, but are not limited to, for example, ethenyl, propenyl, butenyl, 1-methyl-2-buten-1-yl, heptenyl, octenyl, and the like.

The term "alkynyl," as used herein, refer to straight- or branched-chain hydrocarbon radicals containing at least two carbon atoms and preferably from two to eight carbon atoms having at least one carbon-carbon triple bond by the removal of a single hydrogen atom. Representative alkynyl groups include, but are not limited to, for example, ethynyl, 1-propynyl, 1-butynyl, heptynyl, octynyl, and the like.

The term "cycloalkyl" as used herein, refers to a monocyclic or polycyclic saturated carbocyclic ring compound. Examples of cycloalkyl include, but not limited to, cyclopropyl, cyclobutyl, cyclopentyl, cyclohexyl, cycloheptyl and cyclooctyl; bicyclo [2.2.1] heptyl, and bicyclo [2.2.2] octyl.

The term "cycloalkenyl" as used herein, refers to monocyclic or polycyclic carbocyclic ring compound having at least one carbon-carbon double bond. Examples of cycloalkenyl include, but not limited to, cyclopropenyl, cyclobutenyl, cyclopentenyl, cyclohexenyl, cycloheptenyl, cyclooctenyl, and the like.

It is understood that any alkyl, alkenyl, alkynyl and cycloalkyl moiety described herein can also be an aliphatic group as defined above, an alicyclic group or a heterocyclic group.

The term "alicyclic," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo [2.2.1] heptyl, and bicyclo [2.2.2] octyl. Such alicyclic groups may be further substituted.

The terms "heterocyclic" or "heterocycloalkyl" can be used interchangeably and referred to a non-aromatic ring or a bi- or tri-cyclic group fused system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted. Representative heterocyclic groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted.

The term "substituted" refers to substitution by independent replacement of one, two, or three or more of the hydrogen atoms on a moiety such as an aromatic group or an aliphatic group with substituents including, but not limited to, —F, —Cl, —Br, —I, —OH, protected hydroxy, —NO$_2$, —CN, —NH$_2$, protected amino, oxo, thioxo, steroidal, —NH—C$_1$-C$_{12}$-alkyl, —NH—C$_2$-C$_8$-alkenyl, —NH—C$_2$-C$_8$-alkynyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_8$-alkenyl, —O—C$_2$-C$_8$-alkynyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_8$-alkenyl, —C(O)—C$_2$-C$_8$-alkynyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_8$-alkenyl, —CONH—C$_2$-C$_8$-alkynyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_8$-alkenyl, —OCO$_2$—C$_2$-C$_8$-alkynyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_8$-alkenyl, —OCONH—C$_2$-C$_8$-alkynyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_8$-alkenyl, —NHC(O)—C$_2$-C$_8$-alkynyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_8$-alkenyl, —NHCO$_2$—C$_2$-C$_8$-alkynyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, —NHC(O)NH—C$_1$-C$_{12}$-alkyl, —NHC(O)NH—C$_2$-C$_8$-alkenyl, —NHC(O)NH—C$_2$-C$_8$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_8$-alkenyl, —NHC(S)NH—C$_2$-C$_8$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_8$-alkenyl, —NHC(NH)NH—C$_2$-C$_8$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_8$-alkenyl, —NHC(NH)—C$_2$-C$_8$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_8$-alkenyl, —C(NH)NH—C$_2$-C$_8$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_8$-alkenyl, —S(O)—C$_2$-C$_8$-alkynyl, —S(O)—C$_3$-C$_{12}$-cycloalkyl, —S(O)-aryl, —S(O)-heteroaryl, —S(O)-heterocycloalkyl-SO$_2$NH$_2$, —SO$_2$NH—C$_1$-C$_{12}$-alkyl, —SO$_2$NH—C$_2$-C$_8$-alkenyl, —SO$_2$NH—C$_2$-C$_8$-alkynyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_8$-alkenyl, —NHSO$_2$—C$_2$-C$_8$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_8$-alkenyl, —S—C$_2$-C$_8$-alkynyl, —S—C$_3$-C$_{12}$-cycloalkyl, —S-aryl, —S-heteroaryl, —S-heterocycloalkyl, or methylthiomethyl. It is understood that the aryls, heteroaryls, alkyls, steroidals and the like can be further substituted.

The term "halogen," as used herein, refers to an atom selected from fluorine, chlorine, bromine and iodine.

The term "steroidal", as used herein, refers to any of numerous naturally occurring or synthetic fat-soluble organic compounds having as a basis 17 carbon atoms arranged in four rings and including the sterols and bile acids, adrenal and sex hormones, certain natural drugs such as digitalis compounds, and the precursors of certain vitamins. Examples of steroidal structure include, but are not limited to, cholesterol, cholestanol, 3α-cyclo-5-α-cholestan-6-β-ol, cholic acid, cholesteryl formiate, cholestanyl formiate.

For purposes of the invention, the term "short nucleotide(s)" refers to a mono, di or polynucleoside formed from 1 to about 6 linked nucleoside units. Such short nucleotides can be obtained from existing nucleic acid sources, including genomic or cDNA, but are preferably produced by synthetic methods. The nucleoside residues can be coupled to each other by any of the numerous known internucleoside linkages. Such internucleoside linkages may be modified or unmodified and include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "short nucleotide" also encompasses polynucleosides having one or more stereospecific internucleoside linkage (e.g., (R$_P$)- or (S$_P$)-phosphorothioate, alkylphosphonate, or phosphotriester linkages. The short nucleotides of the invention include any such internucleoside linkage, whether or not the linkage comprises a phosphate group. In certain preferred embodiments, these internucleoside linkages may be modified or unmodified and include without limitation, phosphodiester, phosphorothioate, or phosphorodithioate linkages, or combinations thereof.

The term "short nucleotide(s)" also encompasses additional substituents including, without limitation, protein groups, lipophilic groups, intercalating agents, diamines, folic acid, cholesterol and adamantane.

The term "short nucleotide(s)" also encompasses any other nucleobase containing polymers, including, without limitation, peptide nucleic acids (PNA), peptide nucleic acids with phosphate groups (PHONA), locked nucleic acids (LNA). Examples of PNA and LNA are shown below:

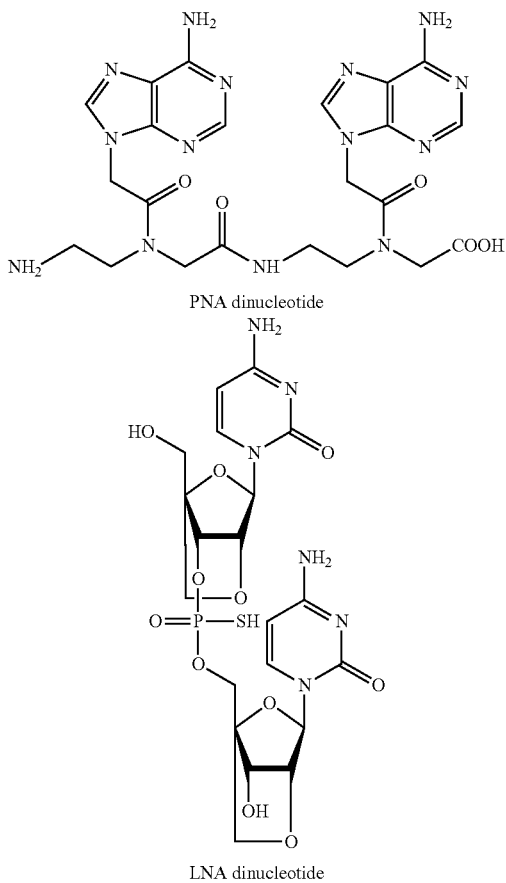

A "nucleotide" refers to a sub-unit of a nucleic acid (whether DNA or RNA or analogue thereof) which includes an internucleotide linkage, a sugar group and a heterocyclic base, as well as analogs of such sub-units. A "nucleoside" references a nucleic acid subunit including a sugar group and a heterocyclic base. It will be appreciated that, as used herein, the terms "nucleoside" and "nucleotide" will include those moieties which contain not only the naturally occurring internucleotide linkages (with respect to "nucleotides") such as phosphodiester internucleotide linkage; naturally occurring sugar moieties such as a ribose and deoxyribose moieties; and naturally occurring nucleobases such as purine and pyrimidine bases, e.g., adenine (A), thymine (T), cytosine (C), guanine (G), or uracil (U), but also modified internucleotide linkages, modified sugar moieties and modified purine and pyrimidine bases or analogs thereof or any combination of modified and unmodified internucleotide linkage, sugar moiety and purine and pyrimidine bases. Other examples of modified nucleosides include acyclonucleosides, which consists of ring-opened versions of the ribose and deoxyribose moieties. Correspondingly, such ring opened nucleosides may be used in forming modified nucleotides. Other examples of modified nucleosides include C-nucleosides such as pseudoisocytidine, and nucleoside mimics including nucleoside isosteres such as peptide nucleic acid monomers.

Modifications of naturally occurring purine and pyrimidine nucleobases include but are not limited to methylated purines or pyrimidines, acylated purines or pyrimidines, and the like, or the addition of a protecting group such as acetyl, difluoroacetyl, trifluoroacetyl, isobutyryl, benzoyl, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N-6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl) uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine, 2,6-diaminopurine 5-trifluoromethyl thymine, 6-chloro-adenine, 7-deaza-adenine.

It should also be understood that a "modified base" also referred to as a "modified nucleobase", includes a nitrogen containing compound that may or may not be heterocyclic. Such preferred nitrogen containing compounds include but are not limited to —$NHR_{18}$ wherein $R_{18}$ is hydrogen, butyloxycarbonyl (Boc), benzyloxycarbonyl, allyl, substituted or unsubstituted alkyl, substituted or unsubstituted cycloalkyl, substituted or unsubstituted aralkyl, substituted or unsubstituted aryl, substituted or unsubstituted heteroaryl, or heterocyclic.

The term "modified base" is further intended to include heterocyclic compounds that that are not nucleosidic bases in the most classical sense but that can serve as nucleosidic bases. Such compounds include "universal bases" as are known in the art. Universal bases may include an aromatic ring moiety, which may or may not contain nitrogen atoms. In some embodiments, a universal base may be covalently attached to the C-1' carbon of a pentose sugar of the nucleoside. Examples of universal bases include 3-methyl-propynylcarbostyryl (PIM), 3-methylisocarbostyryl (MICS), and 5-methyl isocarbostyryl moieties. Additional examples include Inosine derivatives, azole carboxamide analogues, nitroazoles, and nitroimidazoles.

Examples of modified nucleotide and nucleoside sugar moieties include but are not limited to: trehalose, arabinose, 2'-deoxy-2'-substituted pentose moiety, 2'-O-substituted pentose moiety, lyxose, and xylose, or hexose sugar group. For purposes of the invention, the term "2'-substituted" of any of the named sugar groups such as "2' substituted ribonucleoside" or "2'-substituted arabinoside" includes ribonucleosides or arabinonucleoside in which the hydroxyl group at the 2' position of the pentose moiety is substituted to produce a 2'-substituted or 2'-O-substituted ribonucleoside or arabinonucleoside. Preferably, such substitution is with a lower alkyl group containing 1-6 saturated or unsaturated carbon atoms, or with an aryl group having 6-10 carbon atoms, wherein such alkyl, or aryl group may be unsubstituted or may be substituted, e.g., with halo, hydroxy, trifluoromethyl, cyano, nitro, acyl, acyloxy, alkoxy, carboxyl, carboalkoxy, or amino groups. Examples of 2'-O-substituted ribonucleosides or 2'-O-substituted-arabinosides include, without limitation 2'-O-methylribonucleosides (also indicated herein as 2'-OMe) or 2'-O-methylarabinosides and 2'-O-methoxyethylribonucleosides or 2'-O-methoxyethylarabinosides. The term "2'-substituted ribonucleoside" or "2'-substituted arabinoside" also includes ribonucleosides or arabinonucleosides in which the 2'-hydroxyl group is replaced with a lower alkyl group containing 1-6 saturated or unsaturated carbon atoms, or with an amino or halo group. Examples of such 2'-substituted ribonucleosides or 2'-substituted arabinosides include, without limitation, 2'-amino, 2'-fluoro, 2'-allyl, and 2'-propargyl ribonucleosides or arabinosides.

Examples of modified internucleotide linkages include but are not limited to: substituted and unsubstituted phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. Substitutions of modified and unmodified internucleotide linkages include the following moiety:

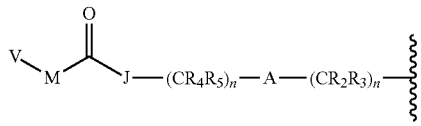

wherein V, M, J, $R_2$, $R_3$, $R_4$, $R_5$ and n are all previously defined in formula I.

The compounds of the present invention contain one or more asymmetric centers and can thus occur as racemates and racemic mixtures, single enantiomers, diastereomeric mixtures and individual diastereomers. The present invention is meant to include short nucleotide compounds having the β-D stereochemical configuration for the five-membered furanose ring, that is, short nucleotide compounds in which the substituents at C-1 and C-4 of the five-membered furanose ring have the β-stereochemical configuration ("up" orientation which is typically denoted by a bold line in some formulas depicted herein).

ABBREVIATIONS

Abbreviations which may be used in the descriptions of the scheme and the examples that follow are:
Ac for acetyl;
AcOH for acetic acid;
$Boc_2O$ for di-tert-butyl-dicarbonate;
Boc for t-butoxycarbonyl;
Bpoc for 1-methyl-1-(4-biphenylyl)ethyl carbonyl;
Bz for benzoyl;
Bn for benzyl;
BocNHOH for tert-butyl N-hydroxycarbamate;
t-BuOK for potassium tert-butoxide;
$Bu_3SnH$ for tributyltin hydride;
CDI for carbonyldiimidazole;
$CH_2Cl_2$ for dichloromethane;
$CH_3$ for methyl;
$CH_3CN$ for acetonitrile;
DMSO for dimethyl sulfoxide;
EtOAc for ethyl acetate;
EtOH for ethanol;
$Et_2O$ for diethyl ether;
HCl for hydrogen chloride;
MeOH for methanol;
MOM for methoxymethyl;
Ms for mesyl or $—SO_2—CH_3$;
$Ms_2O$ for methanesulfonic anhydride or mesyl-anhydride;
NaCl for sodium chloride;
NaH for sodium hydride;
$NaHCO_3$ for sodium bicarbonate or sodium hydrogen carbonate;
$Na_2CO_3$ sodium carbonate;
NaOH for sodium hydroxide;
$Na_2SO_4$ for sodium sulfate;
$NaHSO_3$ for sodium bisulfite or sodium hydrogen sulfite;
$Na_2S_2O_3$ for sodium thiosulfate;
$NH_2NH_2$ for hydrazine;
$NH_4HCO_3$ for ammonium bicarbonate;
$NH_4Cl$ for ammonium chloride;
OH for hydroxyl;
OMe for methoxy;
OEt for ethoxy;
TEA or $Et_3N$ for triethylamine;
TFA trifluoroacetic acid;
THF for tetrahydrofuran;
TPP or $PPh_3$ for triphenylphosphine;
Ts for tosyl or $—SO_2—C_6H_4CH_3$;
$Ts_2O$ for tolylsulfonic anhydride or tosyl-anhydride;
TsOH for p-tolylsulfonic acid;
Ph for phenyl;
TBS for tert-butyl dimethylsilyl;
TMS for trimethylsilyl; or
TMSCl for trimethylsilyl chloride.

Also included within the present invention are pharmaceutical compositions comprising the short oligonucleotide compounds of the invention and derivatives thereof of the present invention in association with a pharmaceutically acceptable carrier. Another example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Another aspect of the present invention provides for the use of the short nucleotide compounds and derivatives thereof and their pharmaceutical compositions for the manufacture of a medicament for the inhibition of a susceptible viral infection in particular HCV replication, and/or the treatment of one or more susceptible viral infections, in particular HCV infection and/or HCV infection in combination with another viral infection such as HBV or HIV. Yet a further aspect of the present invention provides for the short oligonucleotide compounds and derivatives thereof and their pharmaceutical compositions for use as a medicament for the inhibition of RNA-dependent RNA viral replication, in particular HCV replication, and/or for the treatment of RNA-dependent RNA viral infection, in particular HCV infection.

The pharmaceutical compositions of the present invention comprise at least one compound of the invention as an active ingredient or a pharmaceutically acceptable salt thereof, and may also contain a pharmaceutically acceptable carrier and excipients and optionally other therapeutic ingredients. By "pharmaceutically acceptable" is meant that the carrier, diluent, or excipient must be compatible with the other ingredients of the formulation and not deleterious to the recipient thereof. The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor. Various stabilizers may be added that would stabilize the active pharmaceutical ingredient against degradation, such as amino acids or polyamines. Other excipients could include without limitation PEG 400, glycine, Vitamin E derivatives, Sorbitan mono-oleate, Chitosan, Choline citrate, Sorbitan monostearate, Tween 80, Igepal CA 630, Brij 35, NP-40 and their analogous derivatives.

Compounds of the invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous reparation of sterile injectable solutions or dispersions. In all cases, the form is preferably sterile and is preferably fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Any suitable route of administration may be employed for providing a mammal, especially a human with a therapeutically effective dosage of a compound of the present invention. The terms "administration of" and "administering a" compound should be understood to mean providing a compound of the invention to the individual in need. According to the methods of treatment of the present invention, viral infections are treated or prevented in a subject such as a human or lower mammal by administering to the subject a therapeutically effective amount or an inhibitory amount of a compound of the present invention, in such amounts and for such time as is necessary to achieve the desired result. An additional method of the present invention is the treatment of biological samples with an inhibitory amount of a compound of composition of the present invention in such amounts and for such time as is necessary to achieve the desired result.

The term "therapeutically effective amount" of a compound of the invention, as used herein, means a sufficient amount of the compound so as to decrease the viral load in a biological sample or in a subject. As is well understood in the medical arts, a therapeutically effective amount of a compound of this invention will be at a reasonable benefit/risk ratio applicable to any medical treatment.

The term "inhibitory amount" of a compound of the present invention means a sufficient amount to decrease the hepatitis C viral load in a biological sample or a subject. An inhibitory amount or dose of the compounds of the present invention may range from about 0.1 mg/Kg to about 500 mg/Kg, alternatively from about 1 to about 50 mg/Kg. Inhibitory amounts or doses will also vary depending on route of administration, as well as the possibility of co-usage with other agents.

The term "biological sample(s)," as used herein, means a substance of biological origin intended for administration to a subject. Examples of biological samples include, but are not limited to, blood and components thereof such as plasma, platelets, subpopulations of blood cells and the like; organs such as kidney, liver, heart, lung, and the like; sperm and ova; bone marrow and components thereof; or stem cells. Thus, another embodiment of the present invention is a method of treating a biological sample by contacting said biological sample with an inhibitory amount of a compound or pharmaceutical composition of the present invention.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily inhibitory dose of the compounds of this invention administered to a subject in single, multiple or in divided doses can be in amounts, for example, from 0.01 to 50 mg/kg body weight or more usually from 0.1 to 25 mg/kg body weight. Single dose compositions may contain such amounts or submultiples thereof to make up the daily dose. Multiple doses may be single doses taken at different time intervals. In general, treatment regimens according to the present invention comprise administration to a patient in need of such treatment from about 10 mg to about 1000 mg of the compound(s) of this invention per day in single or multiple doses.

Another aspect of the present invention comprises inhibiting or treating HCV infection with a compound of the present invention in combination with one or more agents useful for treating HCV infection. Such agents active against HCV include, but are not limited to: ribavirin, levovirin, viramidine, thymosin alpha-1, interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to: recombinant interferon-α2a (such as Roferon interferon available from Hoffmann-LaRoche, Nutley, N.J.), pegylated interferon-α2a (PEGASYS™), interferon-α2b (such as Intron-A interferon available from Schering Corp., Kenilworth, N.J.), pegylated interferon-α2b (PEGINTRON™), a recombinant consensus interferon (such as interferon alphacon-1), and a purified interferon-α product. Amgen's recombinant consensus interferon has the brand name INFERGEN®. Levovirin is the L-enantiomer of ribavirin which has shown immunomodulatory activity similar to ribavirin. Viramidine represents an analog of ribavirin disclosed in WO 01/60379 (assigned to ICN Pharmaceuticals). In accordance with this method of the present invention, the individual components of the combination can be administered separately at different times during the course of therapy or concurrently in divided or single combination forms. The instant invention is therefore to be understood as embracing all such regimes of simultaneous or alternating treatment, and the term "administering" is to be interpreted accordingly. It will be understood that the scope of combinations of the compounds of this invention with other agents useful for treating HCV infection includes in principle any combination with any pharmaceutical composition for treating HCV infection or an HCV co infection with another virus such as HBV or HIV. When a compound of the present invention or a pharmaceutically acceptable salt thereof is, used in combination with a second therapeutic agent active against HCV, the dose of each compound may be either the same as or different from the dose when the compound is used alone.

For the treatment of HCV infection, the compounds of the present invention may also be administered in combination with an agent that is an inhibitor of HCV NS3 serine protease. HCV NS3 serine protease is an essential viral enzyme and has been described to be an excellent target for inhibition of HCV replication. HCV NS3 protease as a target for the development of inhibitors of HCV replication and for the treatment of HCV infection is discussed in B. W. Dymock, "Emerging therapies for hepatitis C virus infection," Emerging Drugs, 6: 13-42 (2001).

Ribavirin, levovirin, and viramidine may exert their anti-HCV effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly and the monophosphate derivative is an inhibitor of IMPDH. Thus, inhibition of IMPDH represents another useful target for the discovery of inhibitors of HCV replication. Therefore, the compounds of the present invention may also be administered in combination with an inhibitor of IMPDH, [see A. C. Allison and E. M. Eugui, Agents Action, 44 (Suppl.): 165 (1993)].

For the treatment of HCV infection, the compounds of the present invention may also be administered in combination with the antiviral agent amantadine (1-aminoadamantane) [for a comprehensive description of this agent, see J. Kirschbaum, Anal. Profiles Drug Subs. 12: 1-36 (1983)]. The compounds of the present invention may also be combined for the treatment of HCV infection with antiviral 2'-C-branched ribonucleosides disclosed in R. E. Harry-O'kuru, et al., J. Org. Chem., 62: 1754-1759 (1997); M. S. Wolfe, et al., Tetrahedron Lett., 36: 7611-7614 (1995). Such 2'-C-branched ribonucleosides include, but are not limited to: 2'-C-methyl-cytidine, 2'-C-methyl-uridine, 2'-C-methyl-adenosine, 2'-C-methyl-guanosine, and 9-(2-C-methyl-β-D-ribofuranosyl)-2,6-diaminopurine. The compounds of the present invention may also be combined for the treatment of HCV infection with nucleosides having anti-HCV properties. The compounds of the present invention may also be combined for the treatment of HCV infection with non-nucleoside inhibitors of HCV polymerase.

Antiviral compounds which may be used in combination with the compounds of the invention include but are not limited to lamivudine, adefovir, tenofovir, FTC, entecavir, acyclovir, pencyclovir, gancyclovir, interferons, pegylated interferons, ribavirin and other known therapeutic compositions for the treatment of viral infections and viral coinfections such as HCV in combination with HIV and/or HBV.

The invention is further illustrated by the following non-limiting Examples.

EXAMPLE 1

Synthesis of 3'-dApsU$_{2'-OMe}$

In the present studies, the $R_p$,$S_p$ mixture of the phosphorothioate analog 3'-dApsU$_{2'-OMe}$ as shown in Example 2, was synthesized in large scale (I millimol of nucleoside-loaded controlled-pore glass (CPG) support) using solid-phase phosphoramidite chemistry, (Beaucage, S. L.; Iyer, R. P. Tetrahedron 1993, 49, 1925) in conjunction with a specially fabricated LOTUS Reactor® (Padmanabhan, S.; Coughlin, J. E.; Iyer, R. P. Tetrahedron Lett. 2005, 46, 343; Iyer, R. P.; Coughlin, J. E.; Padmanabhan, S. Org. Prep. Proc. Intl. 2005, 37, 205). The dA-linked CPG support was prepared using an ultrafast functionalization and loading process for solid supports. For the sulfurization of the internucleotidic dinucleoside phosphite coupled product, a solution of 3H-1,2-benzodithiole-3-one-1,1-dioxide (0.4 M in dry CH$_3$CN) was employed (Iyer, R. P.; Regan, J. B.; Egan, W.; Beaucage, S. L. J. Am. Chem. Soc. 1990, 112, 1253). Removal of the 5'-trityl group was accomplished by a 2.5% solution of dichloroacetic acid in dichloromethane. Removal of protecting groups at the base, and phosphate and cleavage of the nucleotide from the support was carried out by treating the support-bound product with 28% ammonium hydroxide at room temperature for several hours. Following processing, chromatographic purification, and lyophilization, the sodium salt of $R_p$,$S_p$ 3'-dApsU$_{2'-OMe}$ (~60:40 mixture) was obtained >96% pure, which was characterized by $^{31}$P and $^1$H NMR. $^{31}$P NMR, (D$_2$O), 57.0, and 57.7 ppm.

Alternatively, the title compound could also be prepared by solution-phase method. Typically, 3'-protected 5'-hydroxy Nbz-dA was contacted 5'-DMT-2'-OMe-3'-uridine phosphoramidite in the presence of an activating agent such as tetrazole or thioethyl tetrazole in anhydrous dichloromethane or acetonitrile as solvent in an inert atmosphere. Examples of 3'-protected nucleoside include levulinyl, t-butyldimethylsilyl, benzoyl, 4-t-butylbenzoyl etc. The reaction mixture containing the dinucleoside monophosphite was quenched with water and treated with a solution of a solution of 3H-1,2-benzodithiole-3-one-1,1-dioxide (0.4 M in dry $CH_3CN$) was employed (Iyer, R. P.; Regan, J. B.; Egan, W.; Beaucage, S. L. *J. Am. Chem. Soc.* 1990, 112, 1253). The reaction mixture was detritylated using DCA/DCM and the solution diluted with water, and extracted with dichlormethan. The combined organic layers were washed with $NaHCO_3$, water, and brine. The organic layer was concentrated to obtain the fully protected dinucleoside phosphotriester was processed. Detritylation and removal of the protecting groups was accomplished as before. Following processing, chromatographic purification, and lyophilization, the sodium salt of $R_p, S_p$ 5 (~60:40 mixture) was obtained >96% pure as ascertained by reversed-phase HPLC.

Other dinucleotides claimed in this invention can also be prepared using similar procedures as above. It is pertinent to mention that those skilled in the art will be able to synthesize similar compounds using the classical phosphotriester approach or the H-phosphonate approach (Beaucage, S. L.; Iyer, R. P. *Tetrahedron* 1993, 49, 1925).

EXAMPLE 2

S-isopropylcarbonyloxymethyl thiophosphate (6k) of 3'dApsU$_{2'OMe}$

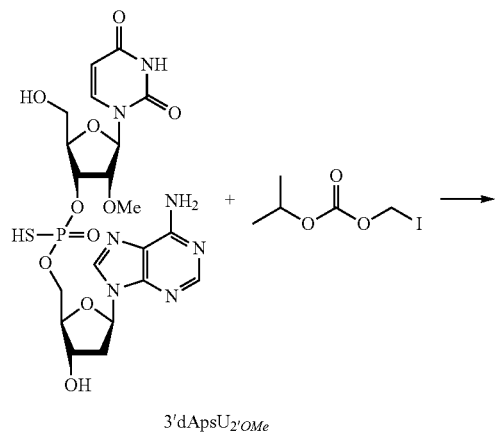

3'dApsU$_{2'OMe}$

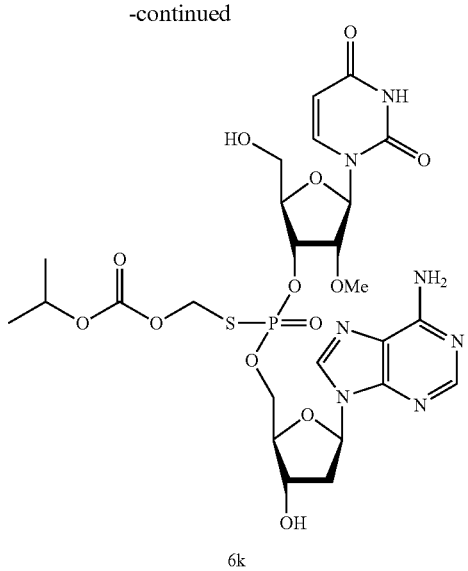

6k

The target compound 6k (also designated Compound 2 in Table 1) is prepared in two steps.

Step 1. Preparation of Iodomethylisopropyl carbonate. To a solution of anhydrous sodium iodide (6 g, 40 mmol) in anhy. acetonitrile (20 mL) chloromethyl isopropyl carbonate (2.9 g, 19 mmol) in anhyd. acetonitrile (10 mL) was added dropwise over 20 min. The reaction mixture, covered with aluminum foil (protected from light) was stirred at room temperature overnight. The solid separated was filtered, washed with acetonitrile and the filtrate was concentrated under reduced pressure. Residue was dissolved in water (10 mL) and organics were extracted in ether (25 mL). Ether extracts were washed with sodium bisulfite (5%, 10 mL), later brine (10 mL). Organic layer was dried over anhd. sodium sulfate, filtered, concentrated and dried under high dried vacuum. Yield 2.72 g (58%); $^1$H-NMR δ 1.3 (d, 6H), 4.95 (m, 1H), 5.95 (s, 2H) ppm.

Step 2. Alkylation of dinucleotide, 3'-ApsU2'OMe. To a solution of dinucleotide of Example 1 (60 mg, 0.098 mmol) in water (HPLC, 400 mL) under stirring, a solution of iodomethyl isopropyl carbonate (80 mg, 0.0166 mmol, 3.33 eq) in acetone (1 mL) was added.

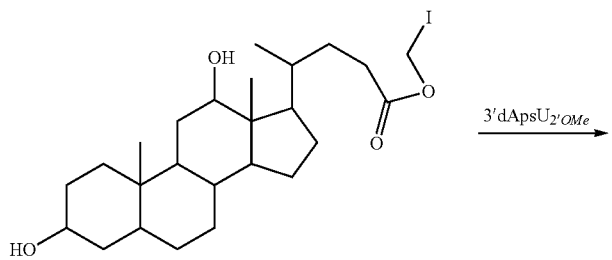

3'dApsU$_{2'OMe}$

-continued

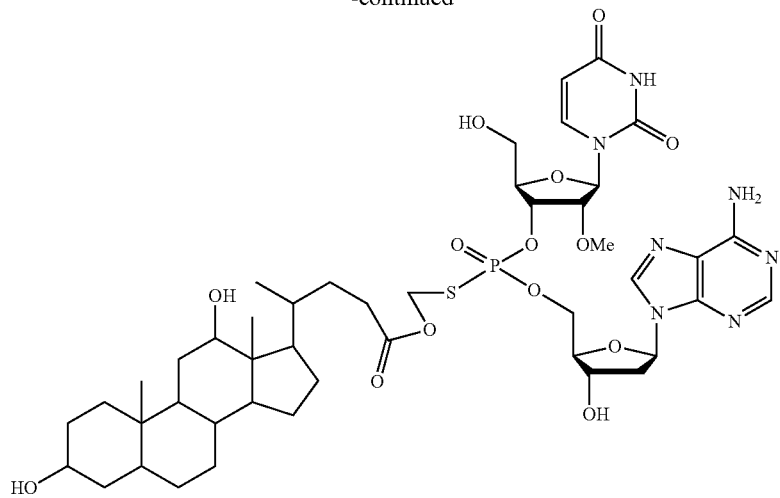

Additional acetone (1 mL) was added to get a clear solution to avoid any separation of oily globules of alkylating agent. The reaction mixture, covered in aluminum foil, was stirred for 3 h, concentrated under rotavap conditions and later in high vacuum to obtain the reaction mixture as a white solid. This was purified by silica column chromatography using initially chloroform and slowly with chloroform containing 2% to finally 8% methanol. The fractions, containing major component, were combined, concentrated and dried under high vacuum overnight. The desired pure product 6k was isolated in almost quantitative yield (68 mg); $^{31}$P-NMR (MeOH-$d_4$) δ 27.7, 28.6.

EXAMPLE 3

Preparation of S-methyl cholic acid ester 61 of 3'dApsU$_{2'OMe}$

Step 1. Synthesis of chloromethyl deoxycholate. To deoxycholic acid (120 mg, 0.306 mmol) in ethanol (4 mL) a solution of caesium carbonate (53 mg, 0.160 mmol) in water (3 mL) was added. The reaction mixture was stirred for 30 min and ethanol was initially removed under rotavap, and later under high vac. The residue was lyophilized to give the cesium salt as white powder. To a solution of cesium salt in N,N-dimethylformamide (DMF, 3 mL) at room temperature bromochloromethane (10 mL) was added and the aluminum foil covered reaction mixture was stirred at room temperature for 24 h. The solvents were removed and the reaction mixture was extracted in dichloromethane (20 mL), washed with water (5 mL), brine (5 mL) and solvent was removed after drying over anhy. sodium sulfate to give the chloromethyl compound (100 mg, 74%). This was used without any further purification for the conversion to the corresponding iodomethyl derivative.

Step 2. Preparation of iodomethyl deoxycholate. To a solution of sodium iodide (304 mg, 2.03 mmol) in anhyd. acetonitrile (3 mL) chloromethyl ester (438 mg, 0.99 mmol) in a mixture of acetonitrile (6 mL) and dichloromethane (2 mL) was added slowly. The reaction mixture, protection from light, was stirred at room temperature over 48 hours. After concentration, the reaction mixture was extracted in dichloromethane (15 mL), organic layer was washed with water (5 mL), sodium bisulfite (5%, 5 mL) and finally brined (5 mL). Dried over anhyd. sodium sulfate and the crude product, obtained after removal of solvent, was purified by silica column chromatography to obtain the iodo compound (110 mg, 21%).

Step 3. Coupling of iodomethyl deoxycholate. To a solution of 3'dApsU2'OMe (50 mg, 0.082 mmol) in water (400 mL) of Example 1, a solution of iodomethyl deoxycholate (110 mg, 2.066 mmol) in acetone (3 mL) was added. The solid separated was dissolved by adding more acetone (~6 mL) and the reaction mixture was stirred overnight. Concentrated under vacuum and purified by silica column chromatography using chloroform to chloroform containing methanol (2 to 10%). Fractions were combined, concentrated and dried under high vacuum to give the desired product 61 (40 mg, 49%); $^{31}$P-NMR (MeOH) δ 28.2, 29.1 ppm.

EXAMPLE 4

Preparation of N-(t-butoxycarbonyl)-L-phenylalaninate (6m)

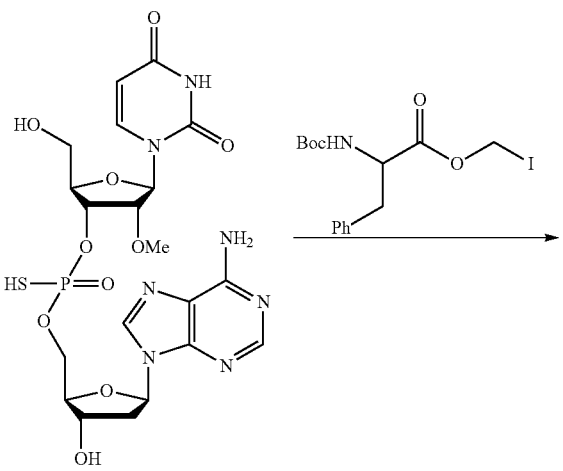

-continued

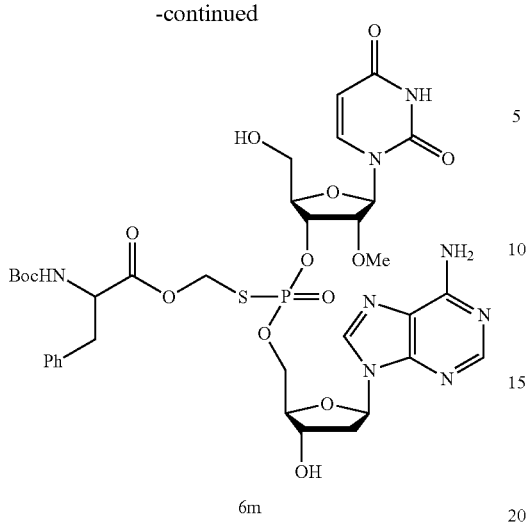

6m

Iodomethyl N-(t-butoxycarbonyl)-L-phenylalaninate. To N-(t-butoxycarbonyl)-L-phenylglycine (663 mg, 2.49 mmol) in ethanol (3 mL) a solution of cesium carbonate (427 mg, 1.31 mmol) in water (2 mL) was added. After the evolution of gas ceased, the reaction mixture was stirred for 1 h. The solvents were removed and lyophilized to obtain the cesium salt. To a solution of cesium salt (270 mg, 0.82 mmol) in N,N-dimethylformamide (DMF, 2 mL) bromochloromethane (5 mL) was added and stirred overnight with the reaction mixture covered with aluminum foil. The solid separated was filtered, washed the solids with DMF (2 mL), and the filtrate concentrated under high vacuum. The product (206 mg, 80%) was found to be pure by TLC (Hex:EtOAc 4:1). This intermediate was used for the conversion to iodo compound without further purification. To a solution of sodium iodide (196 mg, 1.31 mmol) in anhyd. acetonitrile (3 mL), chloromethyl phenylalaniate derivative (206 mg, 0.656 mmol) in anhyd. acetonitrile (1 mL) was added. The reaction mixture was stirred at room temperature, with protection from light, overnight. Filtered, washed the solid with DMF (3 mL), and concentrated the filtrate under vacuum. The residue was extracted in dichloromethane (10 mL) and water (5 mL), washed the organic layer with NaHSO₃ (5%, 5 mL) and brine (satd., 5 mL). The organic layer was dried over anhyd. Na₂SO₄, and concentrated, to yield the desired iodo compound (199 mg, 75%).

Alkylation of 3'dApsU$_{2'OMe}$. To a solution of 3'dApsU2'OMe (44 mg, 0.072 mmol) in water (400 ul) of Example 1, the iodide (100 mg, 0.25 mmol) in acetone (800 ul) was added and the reaction mixture was stirred over night. The reaction mixture was concentrated under vacuum, lyophilized, and purified by silica column chromatography using chloroform and mixture containing chloroform and methanol (2% to 10%). Fractions were collected, combined, concentrated and dried under high vacuum to give the t-Boc protected phenylalanine coupled product 6m (40 mg, 65%); $^{31}$P-NMR (MeOH-d₄) δ 28.7, 27.9 ppm.

EXAMPLE 5

Preparation of 4-acetamidobenzyl derivative 6n of 3'dApsU$_{2'OMe}$

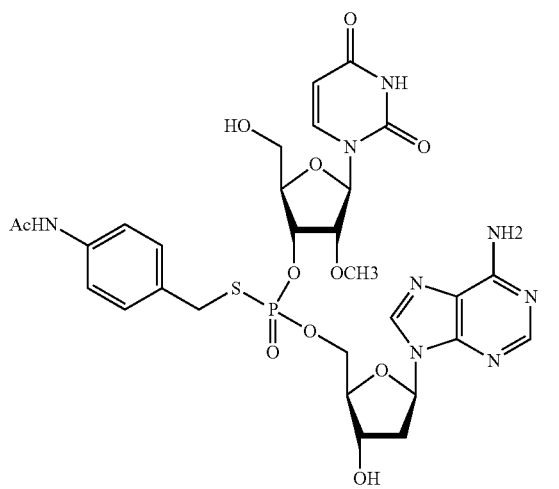

6n

Preparation of 4-acetamidobenzyl alcohol. To a solution of 4-acetamidobenzaldehyde (10 g, 61.3 mmol) in methanol (100 mL) was added sodium borohydride (800 mg) at room temperature in portions. The reaction mixture was stirred over night, and the progress of reaction checked by TLC using 4:1 hexanes:EtOAc as eluent. Absence of starting material indicated the completion of reduction and the reaction mixture was concentrated in a rotavap. The residue was partitioned between water (25 mL) and ethyl acetate (4×50 mL) and the organic layer was washed with brine (25 mL). The ethyl acetate layer was dried over anhydrous sodium sulfate and the removal of the solvent gave the alcohol as a pale yellow solid, which was dried under high vacuum. 8.6 g (85%); $^1$H NMR (DMSO-d₆): δ 2.0 (s, 3H), 4.5 (d, 2H), 5.2 (t, 1H), 7.25 (d, 2H), 7.55 (d, 2H), 9.95 (s, 1H) ppm.

Preparation of 4-acetamidobenzyl iodide. To a cooled solution of anhyd. DMF (5 mL) was added thionyl chloride (0.2 mL, 2.8 mmol). The mixture was stirred for 10 min and a solution of KI (2.49 g, 15 mmol) in anhyd. DMF (12 mL) was added followed by the addition of the alcohol prepared above (0.165 g, 1 mmol). The reaction mixture was stirred in the ice-bath for 3 h and allowed to stir at r.t. overnight. The reaction mixture was poured into ice-water (25 mL) and extracted with ether (3×25 mL). The ether layer was washed with brine, dried over anhyd. sodium sulfate and concentrated to remove the solvent. The product was obtained (138 mg, 50%) as a clean yellow solid. (TLC Hex:EtOAc (1:1). $^1$H NMR (CDCl₃): δ2.17 (s, 3H), 4.45 (s, 2H), 7.17 (br.s, 1H), 7.33 (d, 2H), 7.43 (d, 2H) ppm. This compound was also prepared with improved yields (~75%) using cesium iodide and boron trifluoride etherate in acetonitrile. The coupling of 4-acetamidobenzyl iodide with 3'dApsU2'OMe was done as described for the cholic acid analog before.

EXAMPLE 6

Synthesis of 4-benzamidobutyl analog 6o of 3'dApsU$_{2'OMe}$

EXAMPLE 7

Synthesis of 5-benzoyloxypentyl analog of 3'dApsU$_{2'OMe}$

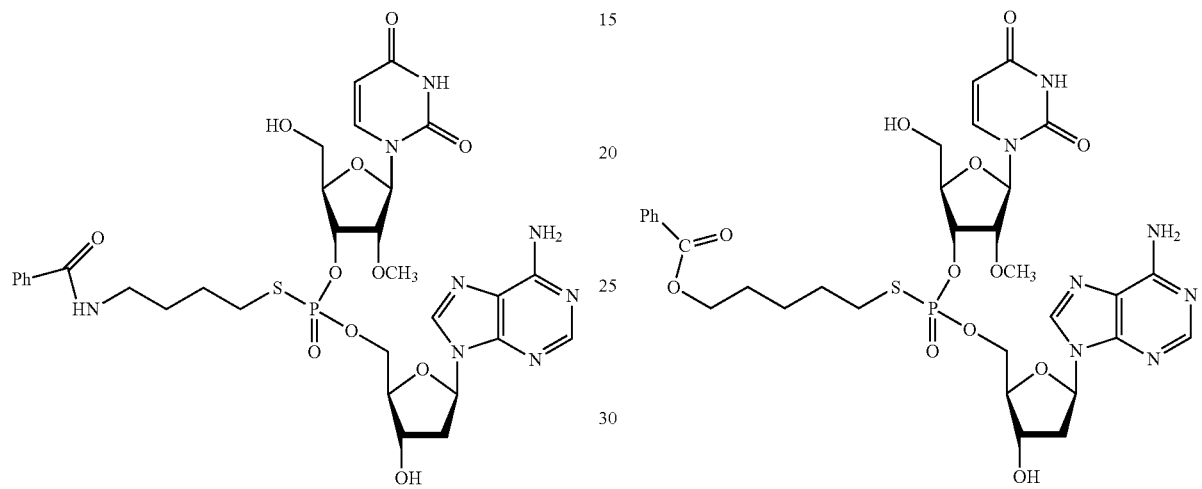

Preparation of 4-benzamidobutyl iodide. To cold anhydrous DMF (5 mL) at 0-5° C. was added thionyl chloride (0.2 mL) and the mixture was stirred for 15 min. A solution of potassium iodide (2.4 g, 5 mmol) in anhy. DMF (8 mL) followed by a solution of 4-benzamidobutanol (193 mg, 1 mmol) in anhy. DMF (2 mL) was added. The colored reaction mixture was stirred overnight. The reaction mixture was worked up by pouring into ice-cold water (~10 mL) and extracted with ether (3×15 mL). Finally, the ether layer was washed with water, brine and dried over anhydrous sodium sulfate. The crude product, obtained after filtration and removal of the solvent, was purified by column chromatography using a mixture of hexane and ethyl acetate (4:1) to give the iodo compound as an oil. 45%; $^1$H NMR (CDCl$_3$): δ 1.77 (m, 2H), 1.93 (m, 2H), 3.23 (t, 2H), 3.55 (q, 2H), 6.26 (br.s, 1H), 7.48 (m, 3H), 7.75 (m, 2H) ppm.

Coupling of the 4-benzamidobutyl iodide with 3'dApsU2'OMe was carried out as before to obtain the title compound 6o.

Preparation of 5-benzoyloxypentan-1-ol. A mixture of benzoic acid (1 g), 1,5-pentanediol (5 mL) and p-toluenesulfonic acid (110 mg) was heated in an oil-bath at 100° C. overnight. The reaction mixture was cooled to room temperature, poured into water (50 mL) and extracted with EtOAc (2×25 mL), washed with sodium carbonated (5%, 20 mL) followed by brine (15 mL). The organic layer was dried over anhyd. sodium sulfate, filtered and concentrated to give almost pure product (1.15 g, 67%).

Preparation of 5-benzoyloxy-1-iodopentane. 36% yield. $^1$H NMR (CDCl$_3$):

δ 1.57 (m, 2H), 1.85 (m, 4H), 3.22 (t, 2H), 4.33 (t, 2H), 7.44 (m, 2H), 7.57 (m, 1H), 8.04 (m, 2H) ppm.

The coupling of 5-benzoyloxy-1-iodopentane with 3'dApsU2'OMe was carried out as before.

Preparation of 5-benzoyloxybutan-1-ol. This was prepared in 73% yield using 1,4-butanediol in the procedure for 5-benzoylpentan-1-ol.

EXAMPLE 8

Synthesis of 4-acetoxybenzyl analog 6q of 3'dApsU$_{2'OMe}$

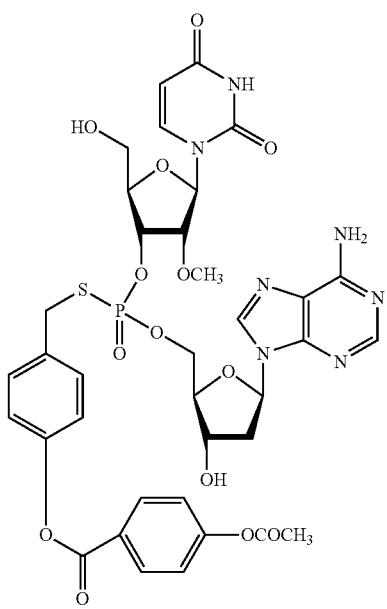

Step 1. Preparation of 4-acetoxybenzyl alcohol. To a cooled suspension of 4-hydroxybenzyl alcohol (1.95 g, 14 mmol) in ethyl acetate (25 mL) in an ice-bath, triethylamine (2.1 mL, 14.9 mmol) was added in one lot under stirring. A solution of acetyl chloride (1.1 mL, 15.5 mmol) in ethyl acetate (12 mL) was added dropwise from an addition funnel. The reaction mixture was stirred overnight. The solid was filtered, washed with ethyl acetate and the residue, after concentration, was purified by column chromatography using hexanes initially and later gradually to 40% ethyl acetate. Yield 40%. $^1$H-NMR (CDCl$_3$), δ 2.02 (br. s, 1H), 2.29 (s, 3H), 4.65 (s, 2H), 7.07 (d, 2H), 7.36 (d, 2H) ppm.

Step 2. Preparation of 4-acetoxybenzyl iodide. To a solution of 4-acetoxybenzyl alcohol (0.332 g, 2 mmol), and cesium iodide (0.571 g, 2.2 mmol) in anhyd. acetonitrile (10 mL) under nitrogen, boron trifluoride etherate (0.28 mL, 2.2 mmol) in acetonitrile (5 mL) was introduced. After stirring overnight, the reaction mixture was poured into ice-cold water (20 mL) and the solid separated was filtered, washed with water and later with hexanes. The product was dried under high vacuum. Yield, 0.39 g, 71%; TLC, hexanes:EtOAC (4:1). $^1$H NMR (CDCl$_3$): δ 2.3 (s, 3H), 4.35 (s, 2H), 7.05 (d, 2H), 7.5 (d, 2H) ppm.

Step 3. Synthesis of 4-acetoxybenzyl analog of 3'dApsU$_{2'OMe}$. Alkylation of 3'dApsU$_{2'OMe}$ with 4-acetoxybenzyl iodide was carried out as before.

EXAMPLE 9

Primary and Secondary Anti-HCV Assays

Primary anti-HCV assay-Antiviral activity against HCV was assessed in a 3-day assay (Okuse, et al., 2005; Antiviral. Res. 65:23; Korba, et al., 2008, Antiviral Res. 77:56) using the stably-expressing HCV replicon cell line, AVA5 [sub-genomic (CON1), genotype 1b](Blight, et al., 2000, Science 290:1972) maintained as sub-confluent cultures on 96-well plates. Antiviral activity was determined by blot hybridization analysis of intracellular HCV RNA (normalized to the level of cellular B-actin RNA in each culture sample). Cytotoxicity was assessed by neutral red dye uptake in cultures maintained in parallel plates.

EC$_{50}$, EC$_{90}$, and CC$_{50}$ values were calculated by linear regression analysis (MS EXCEL®, QUATTROPRO®) using data combined from all treated cultures Korba & Gerin, 1992, Antivir. Res. 19:55; Okuse, et al., 2005, Antivir. Res. 65:23). Standard deviations for EC$_{50}$ and EC$_{90}$ values were calculated from the standard errors generated by the regression analyses. EC$_{50}$ and EC$_{90}$ were drug concentrations at which a 2-fold, or a 10-fold depression of intracellular HCV RNA (relative to the average levels in untreated cultures), respectively was observed. CC$_{50}$ was the drug concentration at which a 2-fold lower level of neutral red dye uptake (relative to the average levels in untreated cultures) was observed. The Selectivity index (S.I.) was calculated as CC$_{50}$/EC$_{50}$. Recombinant human interferon 2b (PBL laboratories, Inc.) was used as an assay control.

Secondary anti-HCV assay—This assay assesses activity against different HCV genotypes using the format described for the primary assay. Activity against the genotype 1b HCV is included for comparison. Currently available is a replicon cell line containing H/FL-Neo (genotype 1a (H77), full length construct) (Blight, et al., 2003, J. Virol. 77:3181). Replicon cell line AVA5 (sub-genomic (CON1), genotype 1b; (Blight, et al., 2000, Science 290:1972).

The results of the primary and secondary assays are shown in Table 3.

TABLE 3

| Compd # | Structure | EC$_{50}$ HCV Type 1A micromolar | EC$_{50}$ HCV type 1B micromolar | EC$_{90}$ HCV type 1A micromolar | EC$_{90}$ HCV type 1B micromolar | CC$_{50}$ micromolar |
|---|---|---|---|---|---|---|
| 2 | 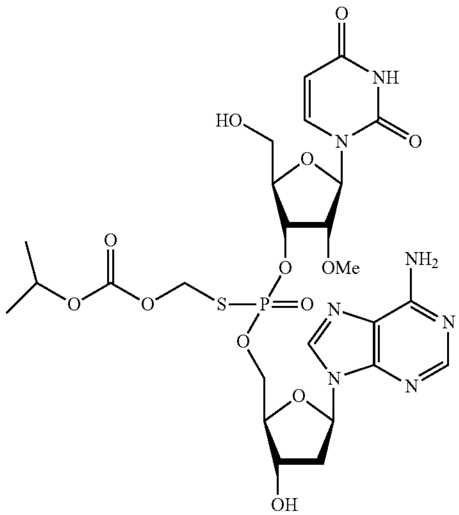 | 2.2 | 1 | 8 | 6 | >100 |
| 1 | 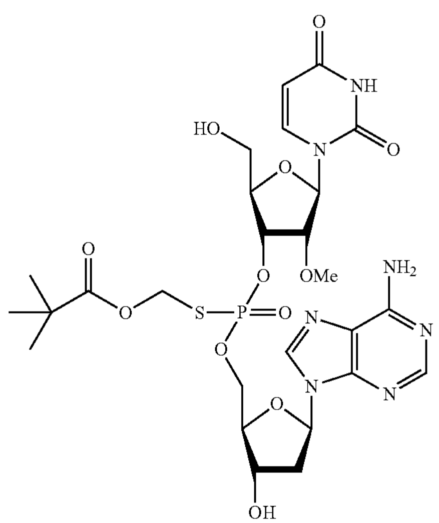 | 2.9 | NA | 8.5 | NA | >100 |
| Interferon (alfNB2)/mL (positive control | | 1.8 | 2 | 8 | 8.5 | >100 |

EXAMPLE 10

Cytotoxicity Assays

Cellular cytotoxicity profile of the compounds was carried out against a panel of cell lines. Standard MTT assays were performed in 96-well plates using the Promega CellTiter96 Non-radioactive Cell Proliferation Assay Kit in conjunction with a 96-well Plate Reader (ThermoMax, Molecular devices), and MDBK, Vero, and HFF cell lines (obtained from ATCC). Several controls were employed including the nucleoside analogs 3TC, AZT, and ddC, as well as, media without drugs. SDS was used as a positive cytotoxic control. The compounds were tested in triplicate at concentrations of 100, 300, and 1000 μM. Following a 24-hour incubation of cells with the test substance, the MTT assay was carried out. The data is shown in Table 4.

TABLE 4

In vitro cytotoxicity studies of compounds in various cell lines

| Compound # | Compound | Vero (CC$_{50}$, uM) | MDBK (CC$_{50}$, uM) | HFF (CC$_{50}$, uM) | HepG2 (CC$_{50}$, uM) |
|---|---|---|---|---|---|
| 2 | [structure] | >1000 | >1000 | >1000 | >100 |
| 1 | [structure] | >1000 | >1000 | >1000 | >100 |

EXAMPLE 11

Inhibition Assays

The effectiveness of the compounds of the present invention as inhibitors of HCV NS5B RNA-dependent RNA polymerase (RdRp) can be measured in the following assay.

Assay for Inhibition of HCV NS5B Polymerase

This assay is used to measure the ability of the compounds of the present invention to inhibit the enzymatic activity of the RNA-dependent RNA polymerase (NS5B) of the hepatitis C virus (HCV) on a heteromeric RNA template.

Procedure:

Assay Buffer Conditions: (50 μL-total/reaction) 20 mM Tris, pH 7.5 50.μM EDTA 5 mM DTT 2 mM MgCl$_2$ 80 mM KCl 0.4 U/μL RNAsin (Promega, stock is 40 units/μL) 0.75 μg t500 (a 500-nt RNA made using T7 runoff transcription with a sequence from the NS2/3 region of the hepatitis C genome) 1.6 μg purified hepatitis C NS5B (form with 21 amino acids C-terminally truncated) 1.μM A,C,U,GTP (Nucleoside triphosphate mix) [alpha-$^{33}$P]-GTP or [alpha$^{32}$P]-GTP.

The compounds are tested at various concentrations up to 100 μM final concentration.

An appropriate volume of reaction buffer is made including enzyme and template t500. Thionucleoside derivatives of the present invention are pipetted into the wells of a 96-well plate. A mixture of nucleoside triphosphates (NTP's), including the radiolabeled GTP, is made and pipetted into the wells of a 96-well plate. The reaction is initiated by addition of the enzyme-template reaction solution and allowed to proceed at room temperature for 1-2 h.

The reaction is quenched by addition of 20 μL 0.5M EDTA, pH 8.0. Blank reactions in which the quench solution is added to the NTPs prior to the addition of the reaction buffer were included.

50 μL of the quenched reaction are spotted onto DE81 filter disks (Whatman) and allowed to dry for 30 min. The filters are washed with 0.3 M ammonium formate, pH 8 (150 mL/wash until the cpm in 1 mL wash is less than 100, usually 6 washes). The filters are counted in 5-mL scintillation fluid in a scintillation counter.

The percentage of inhibition is calculated according to the following equation: % Inhibition=[1−(cpm in test reaction-cpm in blank)/(cpm in control reaction-cpm in blank)]×100.

Counterscreens

The ability of the compounds of the present invention to inhibit human DNA polymerases are measured in the following assays.

a. Inhibition of Human DNA Polymerases Alpha and Beta:

Reaction Conditions:

50 μL reaction volume Reaction Buffer Components: 20 mM Tris-HCl, pH 7.5 200 μg/mL bovine serum albumin 100 mM KCl 2 mM β-mercaptoethanol 10 mM MgCl$_2$ 1.6 μM dA, dG, dC, dTTP α$^{33}$P-dATp Enzyme and Template: 0.05 mg/mL gapped fish sperm DNA template 0.01 U/μL DNA polymerase α or β Preparation of Gapped Fish Sperm DNA Template: Add 5 μL 1M MgCl$_2$ to 500 μL activated fish sperm DNA (USB 70076); Warm to 37° C. and add 30 μL of 65 U/μL of exonuclease III (GibcoBRL 18013-011); Incubate 5 min at 37° C.; Terminate reaction by heating to 65° C. for 10 min; Load 50-100 μL aliquots onto Bio-spin 6 chromatography columns (Bio-Rad 732-6002) equilibrated with 20 mM Tris-HCl, pH 7.5; Elute by centrifugation at 1,000.times.g for 4 min; Pool eluate and measure absorbance at 260 nm to determine concentration.

The DNA template is diluted into an appropriate volume of 20 mM Tris-HCl, pH 7.5 and the enzyme is diluted into an appropriate volume of 20 mM Tris-HCl, containing 2 mM β-mercaptoethanol, and 100 mM KCl. Template and enzyme are pipetted into microcentrifuge tubes or a 96 well plate. Blank reactions excluding enzyme and control reactions excluding test compound are also prepared using enzyme dilution buffer and test compound solvent, respectively. The reaction is initiated with reaction buffer with components as listed above. The reaction wars incubated for 1 hour at 37° C. The reaction was quenched by the addition of 20 μL 0.5M EDTA. 50 μL of the quenched reaction is spotted onto Whatman DE81 filter disks and air dried. The filter disks are repeatedly washed with 150 mL 0.3M ammonium formate, pH 8 until 1 mL of wash is <100 cpm. The disks are washed twice with 150 mL absolute ethanol and once with 150 mL anhydrous ether, dried and counted in 5 mL scintillation fluid.

The percentage of inhibition is calculated according to the following equation: % inhibition=[1−(cpm in test reaction-cpm in blank)/(cpm in control reaction-cpm in blank)]×100.

Inhibition of Human DNA Polymerase Gamma:

The potential for inhibition of human DNA polymerase gamma is measured in reactions that included 0.5 ng/μL enzyme; 10 μM DATP, dGTP, dCTP, and TTP; 2 μCi/reaction [α$^{33}$P]-dATP, and 0.4 μg/μL activated fish sperm DNA purchased from US Biochemical) in a buffer containing 20 mM Tris pH8, 2 mM β-mercaptoethanol, 50 mM KCl, 10 mM MgCl$_2$, and 0.1 μg/μL BSA. Reactions are allowed to proceed for 1 h at 37° C. and were quenched by addition of 0.5 M EDTA to a final concentration of 142 mM. Product formation is quantified by anion exchange filter binding and scintillation counting. Compounds were tested at up to 50 μM.

The percentage of inhibition was calculated according to the following equation: % inhibition=[1−(cpm in test reaction-cpm in blank)/(cpm in control reaction-cpm in blank)]×100.

The ability of the compounds of the present invention to inhibit HIV infectivity and HIV spread is measured in the following assays.

HIV Infectivity Assay:

Assays are performed with a variant of HeLa Magi cells expressing both CXCR4 and CCR5 selected for low background β-galactosidase (β-gal) expression. Cells are infected for 48 h, and β-gal production from the integrated HIV-1 LTR promoter was quantified with a chemiluminescent substrate (Galactolight Plus, Tropix, Bedford, Mass.) Inhibitors were titrated (in duplicate) in twofold serial dilutions starting at 100 μM; percent inhibition at each concentration is calculated in relation to the control infection.

Inhibition of HIV Spread:

The ability of the compounds of the present invention to inhibit the spread of the human immunedeficiency virus (HIV) is measured by the method described in U.S. Pat. No. 5,413,999 (May 9, 1995), and J. P. Vacca, et al., Proc. Natl. Acad. Sci., 91: 4096-4100 (1994), which are incorporated by reference herein in their entirety.

The following assays were employed to measure the activity of the compounds of the present invention against other RNA-dependent RNA viruses: Determination of In Vitro Antiviral Activity of Compounds Against Rhinovirus (Cytopathic Effect Inhibition Assay); assay conditions are described in the article by Sidewall and Huffman, "Use of disposable microtissue culture plates for antiviral and interferon induction studies," Appl. Microbiol. 22: 797-801 (1971).

Viruses:

Rhinovirus type 2 (RV-2), strain HGP, is used with KB cells and media (0.1% NaHCO$_3$, no antibiotics) as stated in the Sidwell and Huffman reference. The virus, obtained from the ATCC, is from a throat swab of an adult male with a mild acute febrile upper respiratory illness.

Rhinovirus type 9 (RV-9), strain 211, and rhinovirus type 14 (RV-14), strain Tow, are also obtained from the American Type Culture Collection (ATCC) in Rockville, Md. RV-9 is from human throat washings and RV-14 is from a throat swab of a young adult with upper respiratory illness. Both of these viruses are used with HeLa Ohio-1 cells (Dr. Fred Hayden, Univ. of VA) which are human cervical epitheloid carcinoma cells. MEM (Eagle's minimum essential medium) with 5% Fetal Bovine serum (FBS) and 0.1% NaHCO$_3$ is used as the growth medium.

Antiviral test medium for all three virus types was MEM with 5% FBS, 0.1% NaHCO$_3$, 50 μg gentamicin/mL, and 10 mM MgCl$_2$.

2000 μg/mL is the highest concentration used to assay the compounds of the present invention. Virus is added to the assay plate approximately 5 min after the test compound. Proper controls are also run. Assay plates are incubated with humidified air and 5% CO$_2$ at 37° C. Cytotoxicity is monitored in the control cells microscopically for morphologic changes. Regression analysis of the virus CPE data and the toxicity control data gave the ED50 (50% effective dose) and CC50 (50% cytotoxic concentration). The selectivity index (SI) is calculated by the formula: SI=CC50/ED50.

Determination of In Vitro Antiviral Activity of Compounds Against Dengue, Banzi, and Yellow Fever (CPE Inhibition Assay.

Assay details are provided in the Sidewall and Huffman reference above.

Viruses:

Dengue virus type 2, New Guinea strain, is obtained from the Center for Disease Control. Two lines of African green monkey kidney cells are used to culture the virus (Vero) and to perform antiviral testing (MA-104). Both Yellow fever virus, 17D strain, prepared from infected mouse brain, and Banzi virus, H 336 strain, isolated from the serum of a febrile boy in South Africa, are obtained from ATCC. Vero cells are used with both of these viruses and for assay.

Cells and Media:

MA-104 cells (BioWhittaker, Inc., Walkersville, Md.) and Vero cells (ATCC) are used in Medium 199 with 5% FBS and 0.1% $NaHCO_3$ and without antibiotics. Assay medium for dengue, yellow fever, and Banzi viruses is MEM, 2% FBS, 0.18% $NaHCO_3$ and 50 μg gentamicin/mL.

Antiviral testing of the compounds of the present invention is performed according to the Sidewall and Huffman reference and similar to the above rhinovirus antiviral testing. Adequate cytopathic effect (CPE) readings are achieved after 5-6 days for each of these viruses.

Determination of In Vitro Antiviral Activity of Compounds Against West Nile Virus (CPE Inhibition Assay).

Assay details are provided in the Sidewall and Huffman reference cited above. West Nile virus, New York isolate derived from crow brain, is obtained from the Center for Disease Control. Vero cells are grown and used as described above. Test medium is MEM, 1% FBS, 0.1% $NaHCO_3$ and 50 μg gentamnicin/mL.

Antiviral testing of the compounds of the present invention is performed following the methods of Sidewall and Huffman, which are similar to those used to assay for rhinovirus activity. Adequate cytopathic effect (CPE) readings are achieved after 5-6 days.

Determination of In Vitro Antiviral Activity of Compounds Against Rhino, Yellow Fever, Dengue, Banzi, and West Nile Viruses (Neutral Red Uptake Assay)

After performing the CPE inhibition assays above, an additional cytopathic detection method is used which is described in "Microtiter Assay for Interferon: Microspectrophotometric Quantitation of Cytopathic Effect," Appl. Environ. Microbiol. 31: 35-38 (1976). A Model EL309 microplate reader (Bio-Tek Instruments Inc.) is used to read the assay plate. ED50's and CD50's were calculated as above.

EXAMPLE 12

Synergistic Antiviral Activity of Compound 2 in Combination with the Anti-HCV Compounds, Ribavirin, Interferon, Nucleoside Analog 2'CmeC and Protease Inhibitor VX-950

Combination treatments of Compound 2 of Table 1 (also referred to in the schemes as 6k) with interferon, ribavirin, VX-950 (protease inhibitor), and 2'CmeCyt (polymerase inhibitor) were carried out using the primary replicon assay as described in Example 9. Briefly, two agents were mixed together at a predetermined relative ratios of the individual agents based on the $EC_{90}$ values of each compound (drug concentrations at which a 10-fold reduction of HCV RNA is observed). For each combination of agents, three concentration ratios, centered on the use of the compounds at equipotent antiviral concentrations, were used. A dilution series (six three-fold-concentration steps, beginning at the approximate $EC_{90}$) was then generated with the concentration ratio of the two agents remaining the same in each dilution step. Toxicity analysis was performed as described above for the monotherapies. Analysis of drug interactions in the combination studies was determined by the use of the CALCUSYN program (Biosoft, Inc., Cambridge, United Kingdom). This program evaluates synergy, additivity, or antagonism by use of several methodologies, including that of Chou and Talalay with a statistical analysis employing the Monte Carlo technique to provide confidence limits, fraction-affected-confidence interval (FA-CI) plots, isobolograms, and median-effect plots. (Belenkii, M. S. Schinazi, R. A method for the analysis of combination therapies with statistical analysis. *Antiviral Res.* 25, 11, 2005). The data is shown in Table 5.

TABLE 5

| Cmpd # | Geno-type | CC50 | EC50 | EC90 | SI | Control 1: alFNB2 (IU/mL) CC50 | EC50 | EC90 | SI | Control 2 (μM) Drug | CC50 | EC50 | EC90 | SI | Comment |
|---|---|---|---|---|---|---|---|---|---|---|---|---|---|---|---|
| 2 (6k) | 1B | >100 | >2.3 | 8.9 | >43 | >10000 | 2.1 | 6.7 | >4762 | 2'CmeCyt | >300 | 1.4 | 5.3 | >214 | |
| 2 + ribavirin | 1B | >100 | >2.3 | 8.8 | >43 | >10000 | 2.1 | 6.7 | >4762 | 2'CmeCyt | >300 | 1.4 | 5.3 | >214 | synergistic interaction |
| 2 + interferon @ 1:1 | 1B | >100 | >0.643 | 2.9 | >156 | >10000 | 2.1 | 6.7 | >4762 | 2'CmeCyt | >300 | 1.4 | 5.3 | >214 | synergistic interaction |
| 2 + interferon @ 1:1 + 30 uM ribavirin | 1B | >100 | >0.629 | 2.6 | >159 | >10000 | 2.1 | 6.7 | >4762 | 2'CmeCyt | >300 | 1.4 | 5.3 | >214 | synergistic interaction |
| 2 + interferon @ 1:3 | 1B | >100 | >0.658 | 2.8 | >152 | >10000 | 2.1 | 6.7 | >4762 | 2'CmeCyt | >300 | 1.4 | 5.3 | >214 | synergistic interaction |
| 2 + interferon @ 1:3 + 30 uM ribavirin | 1B | >100 | >0.686 | 2.5 | >146 | >10000 | 2.1 | 6.7 | >4762 | 2'CmeCyt | >300 | 1.4 | 5.3 | >214 | synergistic interaction |
| 2 + interferon @ 3:1 | 1B | >100 | >0.662 | 2.8 | >151 | >10000 | 2.1 | 6.7 | >4762 | 2'CmeCyt | >300 | 1.4 | 5.3 | >214 | synergistic interaction |
| 2 + interferon @ 3:1 + 30 uM ribavirin | 1B | >100 | >0.777 | 2.7 | >129 | >10000 | 2.1 | 6.7 | >4762 | 2'CmeCyt | >300 | 1.4 | 5.3 | >214 | synergistic interaction |
| 2 + 2'CmeC@1:1 | 1B | >100 | >0.494 | 1.8 | >202 | >10000 | 2.1 | 6.7 | >4762 | 2'CmeCyt | >300 | 1.4 | 5.3 | >214 | synergistic interaction |
| 2 + 2'CmeC@1:3 | 1B | >100 | >0.462 | 1.5 | >216 | >10000 | 2.1 | 6.7 | >4762 | 2'CmeCyt | >300 | 1.4 | 5.3 | >214 | synergistic interaction |
| 2 + 2'CmeC@3:1 | 1B | >100 | >0.552 | 1.3 | >192 | >10000 | 2.1 | 6.7 | >4762 | 2'CmeCyt | >300 | 1.4 | 5.3 | >214 | synergistic interaction |
| 2 + VX-950@10:1 | 1B | >100 | >0.118 | 0.928 | >847 | >10000 | 2.1 | 6.7 | >4762 | VX-950 | 88 | 0.249 | 0.892 | 353 | synergistic interaction |
| 2 + VX-950@100:1 | 1B | >100 | >0.108 | 0.952 | >926 | >10000 | 2.1 | 6.7 | >4762 | VX-950 | 88 | 0.249 | 0.892 | 353 | synergistic interaction |
| 2 + VX-950@30:1 | 1B | >100 | >0.126 | 0.996 | >794 | >10000 | 2.1 | 6.7 | >4762 | VX-950 | 88 | 0.249 | 0.892 | 353 | synergistic interaction |

EXAMPLE 13

In Vitro Bacterial Mutaenicity Assay of the Compound 2

Procedures: Compound 2 was formulated in desiccated dimethylsulfoxide (DMSO) and tested at a maximum concentration of 5000 μg/plate (the standard limit dose for this assay) together with an appropriate number of half-$\log_{10}$ dilutions using the pre-incubation version of the bacterial mutation test. The absence of colonies on sterility check plates confirmed absence of microbial contamination. The mean revertant colony counts for the vehicle controls were close to or within the laboratory historical control range.

Dispense 100 microliter aliquots of the appropriate bacterial cultures into sample tubes stored on ice. Dispense aliquots of the vehicle, positive controls or dose formulations into the appropriate sample tubes. 2 mL top Agar and HBT cap was added to the sample tube, inverted three times and poured into MG plate. The lid was replaced on the plate and left on a level surface to let the agar harden. The plates were incubated in an incubator for 48 to 72 h. The background lawn and count the number of revertants was checked for each plate.

Controls: Appropriate positive control compounds (with S9 mix where required) induced increases in revertant colony numbers to at least twice the concurrent vehicle control levels with the appropriate bacterial strain (1.5× for strain TA100), confirming the sensitivity of the test system and activity of the S9 mix.

Results: No visible thinning of the background lawn of non-revertant bacteria was obtained following exposure to Compound 2, indicating that the test article was non-toxic to the bacteria at the levels tested. No precipitation was observed.

No substantial increases in the revertant colony counts were obtained with any strain following exposure to the test article Compound 2 in either the absence or presence of S9 mix. It is therefore concluded that Compound 2 did not show any evidence of genotoxic activity in this in vitro mutagenicity assay. The data is shown in Tables 6, 7, 8, 9, and 10, below.

TABLE 6

Compound 2 Tested in the Absence of S9

| Strain | Conc. (μg/plate) | S9 | Number of revertants | | | | | Plate observations * | | | Fold response † |
|---|---|---|---|---|---|---|---|---|---|---|---|
| | | | $x_1$ | $x_2$ | $x_3$ | mean | SD | $x_1$ | $x_2$ | $x_3$ | |
| TA1535 | DMSO | 0 | 26 | 23 | 29 | 26 | 3 | | | | 1.0 |
| | 50 | 0 | 10 | 15 | 16 | 14 | 3 | | | | 0.5 A |
| | 158 | 0 | 21 | 26 | 21 | 23 | 3 | | | | 0.9 |
| | 500 | 0 | 15 | 20 | 17 | 17 | 3 | | | | 0.7 |
| | 1581 | 0 | 13 | 18 | 17 | 16 | 3 | | | | 0.6 |
| | 5000 | 0 | 18 | 18 | 17 | 18 | 1 | | | | 0.7 |
| TA1537 | DMSO | 0 | 16 | 15 | 8 | 13 | 4 | | | | 1.0 |
| | 50 | 0 | 8 | 17 | 9 | 11 | 5 | | | | 0.9 |
| | 158 | 0 | 9 | 8 | 19 | 12 | 6 | | | | 0.9 |
| | 500 | 0 | 15 | 6 | 10 | 10 | 5 | | | | 0.8 |
| | 1581 | 0 | 17 | 15 | 13 | 15 | 2 | | | | 1.2 |
| | 5000 | 0 | 15 | 9 | 8 | 11 | 4 | | | | 0.8 |
| TA98 | DMSO | 0 | 31 | 27 | 35 | 31 | 4 | | | | 1.0 |
| | 50 | 0 | 18 | 15 | 33 | 22 | 10 | | | | 0.7 |
| | 158 | 0 | 28 | 28 | 25 | 27 | 2 | | | | 0.9 |
| | 500 | 0 | 21 | 20 | 31 | 24 | 6 | | | | 0.8 |
| | 1581 | 0 | 24 | 18 | 33 | 25 | 8 | | | | 0.8 |
| | 5000 | 0 | 27 | 26 | 20 | 24 | 4 | | | | 0.8 |

* Comments on the plate or background lawn if applicable: contamination (C), incomplete lawn (IL), no lawn (NL), not required (NR), poor lawn (PL), precipitate (ppt)
† Fold response in mean revertants compared to concurrent vehicle control
SD Sample standard deviation (note that SDs based on two values may be unreliable)
A Apparent decreases in colony counts considered to be due to normal variation rather than toxicity since not dose-related and not outside historical control range

TABLE 7

Compound 2 Tested in the Absence of S9

| Strain | Conc. (μg/plate) | S9 | Number of revertants | | | | | Plate observations * | | | Fold response † |
|---|---|---|---|---|---|---|---|---|---|---|---|
| | | | $x_1$ | $x_2$ | $x_3$ | mean | SD | $x_1$ | $x_2$ | $x_3$ | |
| TA100 | DMSO | 0 | 101 | 126 | 106 | 111 | 13 | | | | 1.0 |
| | 50 | 0 | 98 | 112 | 127 | 112 | 15 | | | | 1.0 |
| | 158 | 0 | 110 | 133 | 119 | 121 | 12 | | | | 1.1 |
| | 500 | 0 | 134 | 127 | 138 | 133 | 6 | | | | 1.2 |
| | 1581 | 0 | 122 | 107 | 109 | 113 | 8 | | | | 1.0 |
| | 5000 | 0 | 98 | 126 | 122 | 115 | 15 | | | | 1.0 |
| WP2 uvrA | DMSO | 0 | 31 | 43 | 40 | 38 | 6 | | | | 1.0 |
| | 50 | 0 | 34 | 43 | 45 | 41 | 6 | | | | 1.1 |
| | 158 | 0 | 49 | 44 | 33 | 42 | 8 | | | | 1.1 |
| | 500 | 0 | 39 | 26 | 38 | 34 | 7 | | | | 0.9 |

TABLE 7-continued

Compound 2 Tested in the Absence of S9

| Strain | Conc. (μg/plate) | S9 | $x_1$ | $x_2$ | $x_3$ | mean | SD | $x_1$ | $x_2$ | $x_3$ | Fold response † |
|---|---|---|---|---|---|---|---|---|---|---|---|
| | 1581 | 0 | 44 | 56 | 51 | 50 | 6 | | | | 1.3 |
| | 5000 | 0 | 62 | 39 | 54 | 52 | 12 | | | | 1.4 |

\* Comments on the plate or background lawn if applicable: contamination (C), incomplete lawn (IL), no lawn (NL), not required (NR), poor lawn (PL), precipitate (ppt).
† Fold response in mean revertants compared to concurrent vehicle control

TABLE 8

Compound 2 - Tested in the Presence of S9

| Strain | Conc. (μg/plate) | S9 | $x_1$ | $x_2$ | $x_3$ | mean | SD | $x_1$ | $x_2$ | $x_3$ | Fold response † |
|---|---|---|---|---|---|---|---|---|---|---|---|
| TA1535 | DMSO | + | 22 | 18 | 29 | 23 | 6 | | | | 1.0 |
| | 50 | + | 21 | 15 | 20 | 19 | 3 | | | | 0.8 |
| | 158 | + | 11 | 20 | 16 | 16 | 5 | | | | 0.7 |
| | 500 | + | 19 | 13 | 20 | 17 | 4 | | | | 0.8 |
| | 1581 | + | 27 | 21 | 17 | 22 | 5 | | | | 0.9 |
| | 5000 | + | 18 | 16 | 16 | 17 | 1 | | | | 0.7 |
| TA1537 | DMSO | + | 16 | 23 | 18 | 19 | 4 | | | | 1.0 |
| | 50 | + | 20 | 17 | 15 | 17 | 3 | | | | 0.9 |
| | 158 | + | 16 | 18 | 21 | 18 | 3 | | | | 1.0 |
| | 500 | + | 25 | 12 | 15 | 17 | 7 | | | | 0.9 |
| | 1581 | + | 18 | 15 | 13 | 15 | 3 | | | | 0.8 |
| | 5000 | + | 11 | 15 | 10 | 12 | 3 | | | | 0.6 |
| TA98 | DMSO | + | 41 | 52 | 45 | 46 | 6 | | | | 1.0 |
| | 50 | + | 43 | 39 | 53 | 45 | 7 | | | | 1.0 |
| | 158 | + | 37 | 48 | 34 | 40 | 7 | | | | 0.9 |
| | 500 | + | 31 | 40 | 46 | 39 | 8 | | | | 0.8 |
| | 1581 | + | 44 | 44 | 46 | 45 | 1 | | | | 1.0 |
| | 5000 | + | 53 | 36 | 43 | 44 | 9 | | | | 1.0 |

\* Comments on the plate or background lawn if applicable: contamination (C), incomplete lawn (IL), no lawn (NL), not required (NR), poor lawn (PL), precipitate (ppt)
† Fold response in mean revertants compared to concurrent vehicle control
SD Sample standard deviation (note that SDs based on two values may be unreliable)

TABLE 9

Compound 2- Tested in the Presence of S9

| Strain | Conc. (μg/plate) | S9 | $x_1$ | $x_2$ | $x_3$ | mean | SD | $x_1$ | $x_2$ | $x_3$ | Fold response † |
|---|---|---|---|---|---|---|---|---|---|---|---|
| TA100 | DMSO | + | 163 | 153 | 113 | 143 | 26 | | | | 1.0 |
| | 50 | + | 111 | 109 | 100 | 107 | 6 | | | | 0.7 |
| | 158 | + | 115 | 133 | 111 | 120 | 12 | | | | 0.8 |
| | 500 | + | 134 | 137 | 108 | 126 | 16 | | | | 0.9 |
| | 1581 | + | 136 | 122 | 121 | 126 | 8 | | | | 0.9 |
| | 5000 | + | 122 | 130 | 126 | 126 | 4 | | | | 0.9 |
| WP2 uvrA | DMSO | + | 37 | 35 | 44 | 39 | 5 | | | | 1.0 |
| | 50 | + | 48 | 43 | 42 | 44 | 3 | | | | 1.1 |
| | 158 | + | 46 | 43 | 40 | 43 | 3 | | | | 1.1 |
| | 500 | + | 36 | 46 | 40 | 41 | 5 | | | | 1.1 |
| | 1581 | + | 52 | 43 | 45 | 47 | 5 | | | | 1.2 |
| | 5000 | + | 61 | 60 | 65 | 62 | 3 | | | | 1.6 |

\* Comments on the plate or background lawn if applicable: contamination (C), incomplete lawn (IL), no lawn (NL), not required (NR), poor lawn (PL), precipitate (ppt)
† Fold response in mean revertants compared to concurrent vehicle control
SD Sample standard deviation (note that SDs based on two values may be unreliable)

TABLE 10

Positive Controls for the Test

| Strain | Treatment | Conc. (μg/plate) | S9 | $x_1$ | $x_2$ | $x_3$ | mean | SD | Fold response † |
|---|---|---|---|---|---|---|---|---|---|
| TA1535 | NaAz | 0.5 | 0 | 340 | 312 | 312 | 321 | 16 | 12 |
| TA1537 | 9AC | 10 | 0 | 728 | 910 | 585 | 741 | 163 | 57 |
| TA98 | 2NF | 1 | 0 | 151 | 114 | 153 | 139 | 22 | 4.5 |
| TA100 | NaAz | 0.5 | 0 | 568 | 569 | 543 | 560 | 15 | 5.0 |
| WP2 uvrA | NQO | 0.5 | 0 | 1090 | 1277 | 1300 | 1222 | 115 | 32 |
| TA1535 | 2AA | 5 | + | 263 | 242 | 257 | 254 | 11 | 11 |
| TA1537 | BaP | 5 | + | 112 | 120 | 160 | 131 | 26 | 7 |
| TA98 | BaP | 5 | + | 267 | 336 | 377 | 327 | 56 | 7 |
| TA100 | BaP | 5 | + | 724 | 910 | 882 | 839 | 100 | 6.0 |
| WP2 uvrA | 2AA | 15 | + | 476 | 357 | 285 | 373 | 96 | 9.6 |

† Fold response in mean revertants compared to concurrent vehicle control
SD Sample standard deviation (note that SDs based on two values may be unreliable)
All positive controls are known mutagens

EXAMPLE 14

Tolerability Study of Compound 2 in uPA SCID (KMT) Mouse

The goals of the current study were to evaluate the tolerability of Compound 2 (drug) in KMT mice over a 14 day dosing period and to determine the pharmacokinetic properties of the drug in the study animals. Two separate groups of animals were treated with vehicle control or with a daily drug dose of 300 mg/kg for 14 days. Blood samples were taken 15 minutes after the drug doses on Day 1 (first dose), Day 7 and Day 14 (last dose) for measurement of the concentration of the drug in the serum of study animals. Body weights and health index scores were monitored daily in order to assess tolerance of the study animals to the dosing procedure and the drug. On each morning of the study one bottle of Compound 2 was dissolved in the 0.05 M citric acid, pH 3.0, vehicle to the required concentration of 40 mg/mL. The solution was used to dose animals in a volume of 7.5 ml/kg. The citric acid buffer was also used for dosing of the vehicle control animals.

Ten KMT transgenic animals with low engraftment of human liver cells (hAAT values less than 20 at 6 weeks) were allocated to this study. Individual body weights of animals were recorded prior to treatment and daily during the study. Animals were also evaluated once a day (at morning dose administration) for clinical signs and monitored for morbidity and mortality. The study animals were allocated into 2 groups of 5 animals. Compound 2 or citric acid vehicle control were administered once a day by oral gavage employing a sterile syringe and feeding needle for each animal. Dosing volume was 7.5 mL/kg (150 μL/20 grams body weight) for all groups. The volume was adjusted based on the daily body weight of each individual animal. Group 1 animals received the citric acid control and Group 2 animals received Compound 2 at 300 mg/kg. The study started on Day 1 with the first drug dose administered in the morning and continued up to Day 14, the last day of drug treatment. Blood was collected via the central tail artery from all animals of each group on Day 1, fifteen minutes after the first drug dose, on Day 7, fifteen minutes after the drug dose, and on Day 14, fifteen minutes after the last drug dose. The blood samples were allowed to clot and the serum removed from above the clot pellet. Serum samples were stored at −80° C. prior to shipment to the study client. The final experimental schedule is summarized below in Table 11.

TABLE 11

Experimental schedule for study NEA-1

| Animal ID/ Group | Day(s) | Date | Manipulation | Blood Volume Required |
|---|---|---|---|---|
| 1-2 | 1 | | Dosing of animals | n/a |
| 1-2 | 1 + 15 min. | | 15 minute PK blood draw | 100 μl |
| 1-2 | 2-7 | | Dosing of animals | n/a |
| 1-2 | 7 + 15 min. | | 15 minute PK blood draw | 100 μl |
| 1-2 | 8-14 | | Dosing of animals | n/a |
| 1-2 | 14 + 15 min. | | 15 minute PK blood draw | 100 μl |

Individual body weights of the animals were recorded prior to treatment and daily during the course of the study. The animals were also evaluated daily for clinical signs and monitored for morbidity and mortality. The standardized scale used to monitor morbidity (health index) of study animals is summarized below in Table 12.

TABLE 12

Mouse morbidity indexing scale

| Index | Attributes |
|---|---|
| 1 | Normal shiny coat, bright eyes, very active, good body condition, grooming, normal behaviour, normal eating/drinking pattern |
| 1-2 | Slightly scruffy coat, dull coat, greasy coat, less active |
| 2 | As above plus slight lethargy, slight dehydration, sunken eyes |
| 2-3 | As above plus increased scruffiness, dehydrated, emaciated, lethargic, slight hunched posture |
| 3 | As above plus extreme non-grooming (terrible coat appearance) bony along spine, hunched posture, emaciated, diarrhea |
| 3-4 | As above plus moribund, requiring euthanasia |
| 4 | Euthanized or found dead |

Compound 2 was generally well tolerated by the study animals. One animal in the vehicle control group exhibited a moderately elevated health index from Day 11 thru Day 14 of the study. Two animals in the drug treatment group also exhibited moderately elevated health index values. All other study animals completed the study with health values that were equal to or half a score greater than their initial values.

Health index values are shown in Table 13.

TABLE 13

Health index values for individual animals in all treatment groups.

| Group | ID # | D1 | D2 | D3 | D4 | D5 | D6 | D7 | D8 | D9 | D10 | D11 | D12 | D13 | D14 |
|---|---|---|---|---|---|---|---|---|---|---|---|---|---|---|---|
| Group 1 | F139 | 1-2 | 1-2 | 1-2 | 1-2 | 1-2 | 1-2 | 2 | 2 | 1-2 | 1-2 | 2 | 2-3 | 2-3 | 2-3 |
| Citrate | F146 | 1-2 | 1-2 | 1-2 | 1-2 | 1-2 | 1-2 | 1-2 | 1-2 | 1-2 | 1-2 | 1-2 | 1-2 | 1-2 | 1-2 |
| Control | F163 | 1-2 | 1 | 1-2 | 1-2 | 1-2 | 1-2 | 1-2 | 1-2 | 1-2 | 1-2 | 1-2 | 1-2 | 1-2 | 1-2 |
|  | F170 | 1 | 1 | 1-2 | 1-2 | 1-2 | 1-2 | 1-2 | 1-2 | 1-2 | 1-2 | 1-2 | 1-2 | 1-2 | 1-2 |
|  | F189 | 1 | 1-2 | 2 | 1-2 | 1-2 | 1-2 | 1-2 | 1-2 | 1-2 | 1-2 | 1-2 | 1-2 | 1-2 | 1-2 |
| Group 2 | F173 | 1-2 | 1-2 | 1-2 | 1-2 | 1-2 | 1-2 | 2 | 1-2 | 2 | 2 | 1-2 | 1-2 | 1-2 | 1-2 |
| Cpd 2 | F165 | 1 | 1 | 1-2 | 1-2 | 1-2 | 1-2 | 1-2 | 1-2 | 1-2 | 1-2 | 1-2 | 1-2 | 1-2 | 1-2 |
| 300 mg/kg | F177 | 1 | 1-2 | 1-2 | 1-2 | 1-2 | 1-2 | 1-2 | 1-2 | 1-2 | 1-2 | 1-2 | 1-2 | 1-2 | 1-2 |
|  | F187 | 1 | 1-2 | 1-2 | 1-2 | 1-2 | 1-2 | 2 | 1-2 | 1-2 | 1-2 | 1-2 | 1-2 | 1-2 | 2 |
|  | F189 | 1 | 1 | 1-2 | 1-2 | 1-2 | 1-2 | 1-2 | 1-2 | 1-2 | 1-2 | 1-2 | 1-2 | 1-2 | 2 |

Two animals in the vehicle control group (F139 and F170) had a marginal net loss in body weight from Day 1 to Day 14 of the study. One animal in the drug group (F187) also showed a small decrease in body weight.

Study procedures, drugs and drug vehicles have varying affects on the health of study animals. In the current study, only 3 of 10 animals showed any degree of adverse impact and, on balance, this was equally distributed between the control and drug groups. Thus, the current dosing regimen and drug dose of 300 mg/kg was well tolerated by animals.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

What is claimed:

1. A method of treating HCV infection comprising administering to a patient in need of such treatment an effective amount of a compound of formula A1:

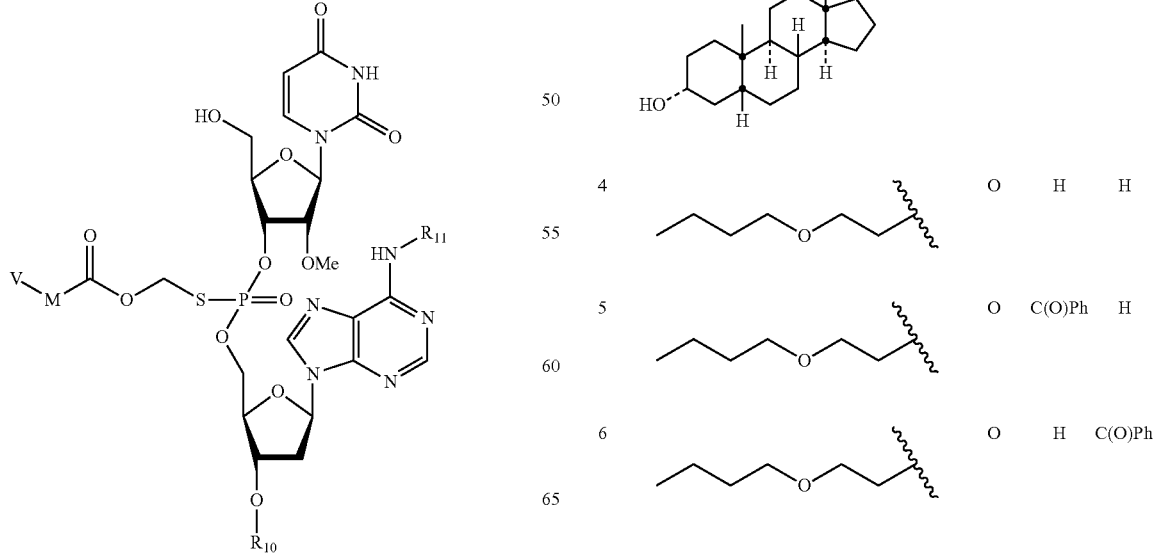

or a pharmaceutically acceptable salt, ester, stereoisomer, tautomers, solvate or combination thereof, wherein V, M, $R_{10}$ and $R_{11}$ are delineated for compounds I-8 in Table 1

TABLE 1-continued

| Compound No. | V | M | $R_{10}$ | $R_{11}$ |
|---|---|---|---|---|
| 7 | ![H2N-CH(CH2Ph)-] | absent | H | H |
| 8 | ![H3CO, HO-C6H3-CH=CH-CO-CH(H)-CO- and -CH=CH-C6H4-OCH3] | O | H | H. |

2. A method of treating HCV infection comprising administering to a patient in need of such treatment an effective amount of a compound of formula B1:

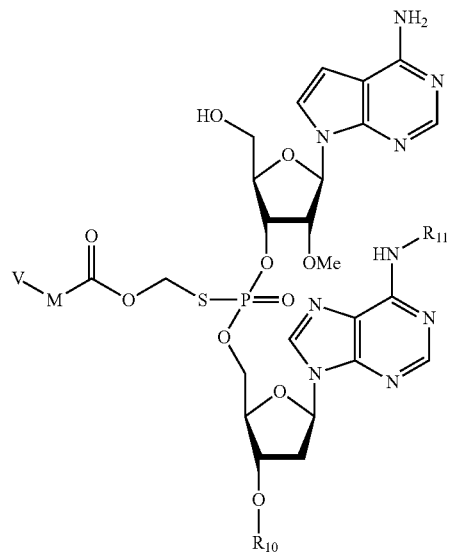

or a pharmaceutically acceptable salt, ester, stereoisomer, tautomers, solvate or combination thereof, wherein V, M, $R_{10}$ and $R_{11}$ are delineated for compounds 9-16 in Table 2:

TABLE 2

| Compound No. | V | M | $R_{10}$ | $R_{11}$ |
|---|---|---|---|---|
| 9 | ![tert-butyl] | absent | H | H |
| 10 | ![isopropyl] | O | H | H |
| 11 | ![cholic acid derivative steroid] | absent | H | H |
| 12 | ![CH3CH2CH2CH2-O-CH2CH2-] | O | H | H |
| 13 | ![CH3CH2CH2CH2-O-CH2CH2-] | O | C(O)Ph | H |
| 14 | ![CH3CH2CH2CH2-O-CH2CH2-] | O | H | C(O)Ph |

TABLE 2-continued

| Compound No. | V | M | $R_{10}$ | $R_{11}$ |
|---|---|---|---|---|
| 15 | H₂N–CH(CH₂Ph)– | absent | H | H |
| 16 | 3-MeO-4-HO-C₆H₃–CH=CH–CO–CH₂–CO–CH=CH–C₆H₃(OMe)– | O | H | H. |

3. The method of claim 1 or 2, wherein the HCV infection is an HCV co-infection with a second virus.

4. The method of claim 3, wherein the second virus is HBV, HIV, Influenza A, Influenza B, West Nile Virus, Dengue Virus, RSV, Rhinovirus.

5. The method of claim 1, wherein said compound is

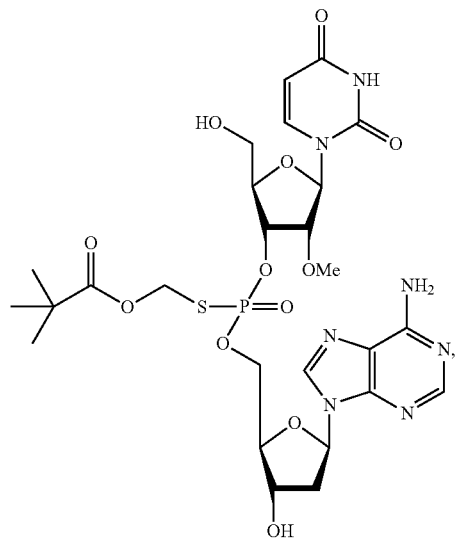

or a pharmaceutically acceptable salt, ester, stereoisomer, tautomers, solvate, or combination thereof.

6. The method of claim 1, wherein said compound is

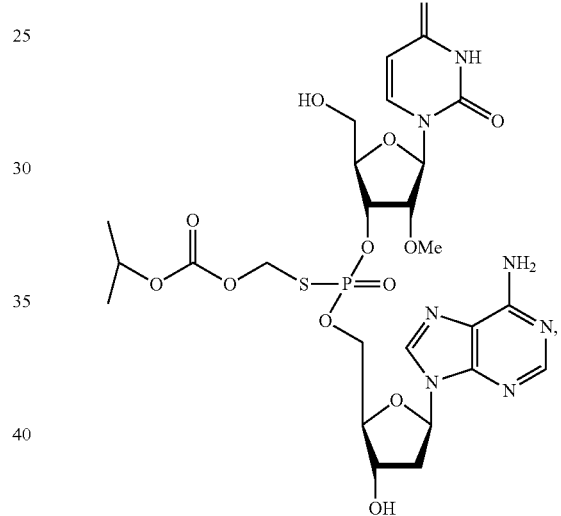

or a pharmaceutically acceptable salt, ester, stereoisomer, tautomers, solvate, or combination thereof.

\* \* \* \* \*